US008101191B2

United States Patent
Jacobs, Jr. et al.

(10) Patent No.: US 8,101,191 B2
(45) Date of Patent: Jan. 24, 2012

(54) MYCOBACTERIAL SECA2 MUTANTS

(75) Inventors: William R. Jacobs, Jr., Pelham, NY (US); Steven A. Porcelli, Bronx, NY (US); Miriam Braunstein, Chapel Hill, NC (US)

(73) Assignees: Albert Einstein College of Medicine of Yeshiva University, Bronx, NY (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 12/087,628

(22) PCT Filed: Jan. 11, 2007

(86) PCT No.: PCT/US2007/000793
§ 371 (c)(1),
(2), (4) Date: Dec. 4, 2008

(87) PCT Pub. No.: WO2007/084353
PCT Pub. Date: Jul. 26, 2007

(65) Prior Publication Data
US 2009/0110696 A1    Apr. 30, 2009

Related U.S. Application Data

(60) Provisional application No. 60/758,944, filed on Jan. 12, 2006.

(51) Int. Cl.
*A61K 39/04* (2006.01)
(52) U.S. Cl. .................. 424/248.1; 435/172.1; 435/243
(58) Field of Classification Search .......... None
See application file for complete search history.

(56) References Cited

U.S. PATENT DOCUMENTS

| | | | |
|---|---|---|---|
| 5,504,005 A | 4/1996 | Bloom et al. |
| 5,736,367 A | 4/1998 | Haun et al. |
| 5,773,267 A | 6/1998 | Jacobs et al. |
| 5,972,700 A | 10/1999 | Jacobs, Jr. et al. |
| 6,268,201 B1 | 7/2001 | Alland et al. |
| 6,271,034 B1 | 8/2001 | Bardarov et al. |
| 6,290,966 B1 | 9/2001 | Cox et al. |
| 6,372,478 B1 | 4/2002 | Bloom et al. |
| 6,387,694 B1 | 5/2002 | McKinney et al. |
| 6,423,545 B1 | 7/2002 | Pavelka, Jr. et al. |
| 6,562,348 B2 | 5/2003 | Hondalus et al. |
| 6,566,121 B1 | 5/2003 | Jacobs, Jr. et al. |
| 6,733,761 B2 | 5/2004 | McKinney et al. |
| 6,752,994 B2 | 6/2004 | Jacobs, Jr. et al. |
| 6,821,769 B2 | 11/2004 | Alland et al. |
| 7,722,861 B2 | 5/2010 | Jacobs et al. |
| 7,758,874 B2 | 7/2010 | Jacobs, Jr. et al. |
| 7,939,089 B2 | 5/2011 | Jacobs et al. |
| 7,998,471 B2 | 8/2011 | Jacobs, Jr. et al. |
| 2003/0059441 A1 | 3/2003 | Pavelka, Jr. et al. |
| 2005/0260232 A1 | 11/2005 | Jacobs et al. |
| 2007/0202131 A1 | 8/2007 | Jacobs, Jr. et al. |
| 2008/0254061 A1 | 10/2008 | Jacobs et al. |
| 2008/0268541 A1 | 10/2008 | Jacobs et al. |
| 2009/0110696 A1 | 4/2009 | Jacobs, Jr. et al. |
| 2010/0297185 A1 | 11/2010 | Jacobs, Jr. et al. |

OTHER PUBLICATIONS

International Preliminary Report on Patentability (1 page) for related application PCT/US2007/000793 with an international filing date of Jan. 11, 2007.
Written Opinion of the International Searching Authority (8 pages) for related application PCT/US2007/000793 with an international filing date of Jan. 11, 2007.
International Search Report (5 pages) for related application PCT/US2007/000793 with an international filing date of Jan. 11, 2007.
Braunstein et al., entitled "SecA2 functions in the secretion of superoxide dismutase A and in the virulence of *Mycobacterium tuberculosis*," Molecular Microbiology, 2003, vol. 48, No. 2, pp. 453-464.
Communication Supplementary European Search Report in connection with European Patent Patent Application No. 07717990.1 dated Dec. 15, 2009, 2 pages.
Hinchey J et al., entitled Enhanced priming of adaptive immunity by a proapoptotic mutant of *Mycovacterium tuberculosis*. The Journal of Clinical Investigation, vol. 117, No. 8, Aug. 2007, pp. 2279-2288.
Sambandamurthy V S et al., entitled "Live attenuated mutants of *Mycobacterium tuberculosis* as candiate vaccines against turberlosis," Microbes and Infection 7 (2006), pp. 955-961.
Ranganthan U D K, et al., entitled Recombinant pro-apoptotic *Mycobacterium tuberculosis* generates CD8+ T cell responses against human immunodeficiency virus typ 1 Env and *M. tuberculosis* in neonatal mice, Vaccine 28 (2010), pp. 152-161.
U.S. Appl. No. 12/450,193, filed on Mar. 10, 2008.

*Primary Examiner* — Jennifer Graser
(74) *Attorney, Agent, or Firm* — Amster, Rothstein & Ebenstein LLP

(57) ABSTRACT

Provided are mycobacteria comprising (a) a mutation that is not in a SecA2 gene that attenuates the virulence of the mycobacteria in a mammalian host, and (b) a mutation in a SecA2 gene that eliminates SecA2 activity. Also provided are mycobacteria that comprise a mutation in a SecA2 gene that eliminates SecA2 activity, where the mycobacteria are not *Mycobacterium tuberculosis* or *Mycobacterium smegmatis*. Additionally provided are methods of inducing an immune response in a mammal and methods of inducing an immune response to a pathogenic *mycobacterium* in a human using the above mycobacterial mutants.

24 Claims, 22 Drawing Sheets

A.

B.

A.

p47$^{phox-/-}$

B.

gp91$^{phox-/-}$

A.

B.

A.

B.

MYCOBACTERIAL SECA2 MUTANTS

CROSS-REFERENCE TO RELATED APPLICATION

This is a U.S. national phase of PCT Application No. PCT/EP2007/000793, filed Jan. 11, 2007, which claims the benefit of U.S. Provisional Application No. 60/758,944, filed Jan. 12, 2006.

STATEMENT REGARDING FEDERALLY SPONSORED RESEARCH OR DEVELOPMENT

The invention was made with government support under grant numbers R01 AI54540, AI26170, AI063537, and AI57158 awarded by the National Institutes of Health. The government has certain rights in the invention.

BACKGROUND OF THE INVENTION (1) Field of the Invention

The present invention generally relates to mycobacterial vaccines. More specifically, the invention is directed to mycobacterial compositions comprising SecA2 mutations and their use in inducing immunity to mycobacteria and other antigens.

(2) Description of the Related Art

*Mycobacterium tuberculosis*, the etiological agent of tuberculosis, is responsible for more deaths each year than any other single pathogen (Corbett et al., 2003). The emergence of drug resistant strains of *M. tuberculosis* and HIV co-infection has contributed to the worsening impact of this disease. The pathogen exhibits extraordinary capacity to subvert and resist bactericidal responses of its infected host. *M. tuberculosis* virulence has been associated with its initial survival within macrophages by evading the host response in many different ways. The tubercle bacilli reside in endocytic vacuoles (Armstrong and Hart, 1975; Clemens and Horwitz, 1995), which fail to fuse to lysosomes due to *M. tuberculosis* mediated retention of a host protein TACO on the membrane of these vacuoles (Gatfield and Pieters, 2000). Similarly, *M. tuberculosis* can downregulate the expression of MHC-II (Noss et al., 2001) and costimulatory molecules (Stenger et al., 1998; Wadee et al., 1995), modulate the cytokine environment in its vicinity (VanHeyningen et al., 1997) and inhibit apoptosis of the host cell (Keane et al., 1997). Although *M. tuberculosis* evades many host responses to maintain itself in a habitable environment, the bacterial effectors mediating such effects need to be delineated. On invading the host cell, a capsule-like structure is formed outside the membrane and the cell wall of the tubercle bacilli (Daffe and Etienne, 1999), and this interface contains important surface proteins involved in the pathogenesis and immune responses to TB. The secreted and cell envelope associated proteins, located at the interface between the mycobacterium and its eukaryotic host mediate host-pathogen interactions. Therefore, such proteins are candidate virulence factors and warrants further study (Finlay and Falkow, 1997).

The exported and secreted proteins of *M. tuberculosis* have been proposed to play a role in virulence and indeed contribute to the immune responses to TB (Abou-Zeid et al., 1988; Johansen et al., 1996; Nagai et al., 1991; Zhang et al., 1992). Research on several bacterial pathogens has revealed that the majority of virulence factors are secreted (Finlay and Falkow, 1997). Studies have also emphasized the importance of the secreted and exported proteins of *M. tuberculosis* in the generation of a protective immune response. The most striking demonstration of this property comes from experiments in which mice or guinea pigs were immunized with extracellular proteins and significant protective immunity elicited (Andersen, 1994; Hubbard et al., 1992; Pal and Horwitz, 1992; Roberts et al., 1995). Recently, the exported ERP (exported repetitive protein) protein was shown to contribute to the virulence of *M. tuberculosis* (Berthet et al., 1998). Likewise, superoxide dismutase (SOD), a culture filtrate component was shown to be associated with virulence by interfering with host apoptosis (Edwards et al., 2001). While many secreted proteins have been studied, the study of the cell surface proteins is still lacking due to technological constraints in isolating samples of membrane proteins.

Host cell apoptosis has been implicated in *Mycobacterium* spp. virulence and protective immunity (e.g., Alemán et al., 2002; Balcewicz-Sablinska et al., 1998; Ciaramella et al., 2000; Duan et al., 2001, 2002; Duarte et al., 1997; Eddine et al., 2005; Grode et al., 2005; Keane et al., 2000; Kornfeld et al., 1999; López et al., 2003; Protales-Pérez et al., 2002; Sly et al., 2003; Spira et al., 2003). However, there is need for more information on *Mycobacterium* host genes that affect host cell apoptosis. The present invention addresses that need.

SUMMARY OF THE INVENTION

Accordingly, the inventors have discovered that the SecA2 protein prevents host cell apoptosis. The inventors have also discovered that mycobacterial mutants that do not express SecA2 improve the ability of the mycobacterium to induce an immune response against virulent mycobacteria or recombinant antigens expressed by the mycobacterium.

Thus, the invention is directed to mycobacteria comprising (a) a mutation that is not in a SecA2 gene, where a wild-type mycobacterium comprising the mutation exhibits attenuated virulence in a mammal when compared with the wild-type mycobacterium without the mutation; and (b) a mutation in a SecA2 gene, wherein the mutation eliminates SecA2 activity.

The invention is also directed to mycobacteria comprising a mutation in a SecA2 gene, where the mutation eliminates SecA2 activity. These mycobacteria are not *Mycobacterium tuberculosis* or *Mycobacterium smegmatis*.

Additionally, the invention is directed to methods of inducing an immune response in a mammal. The methods comprise inoculating the mammal with any of the above-described mycobacteria.

The invention is also directed to methods of inducing an immune response to a pathogenic mycobacterium in a human. The methods comprise inoculating the human with a mycobacterium vaccine. The mycobacterium vaccine comprises a mycobacterium comprising a mutation in a SecA2 gene, where the mutation eliminates SecA2 activity.

DETAILED DESCRIPTION OF THE INVENTION

Figure 1:
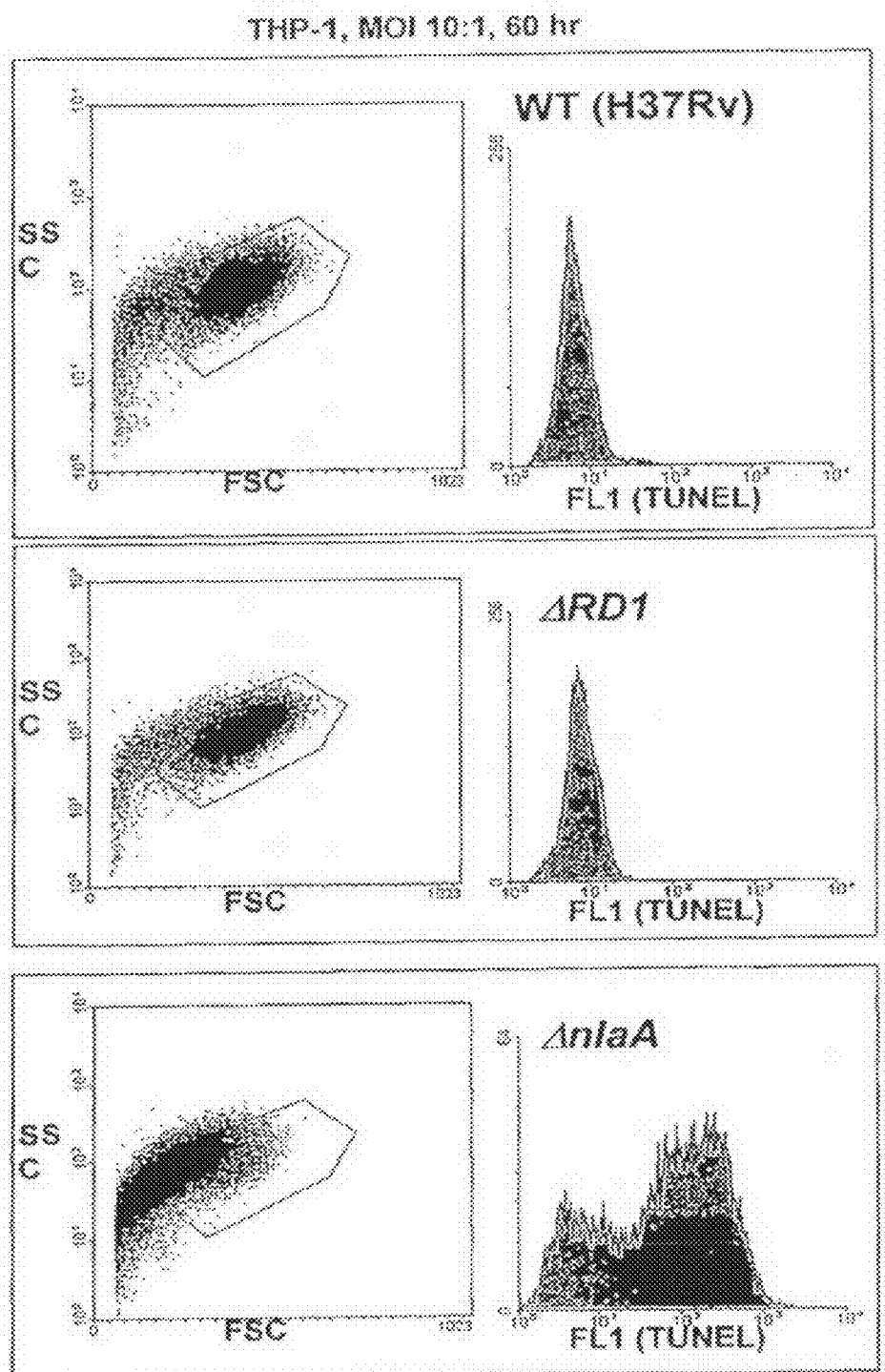
FIG. 1 is graphs of forward light scattering and TUNEL assays showing induction of apoptosis in THP-1 cells by *M. tuberculosis* ΔnlaA.
Figure 2:
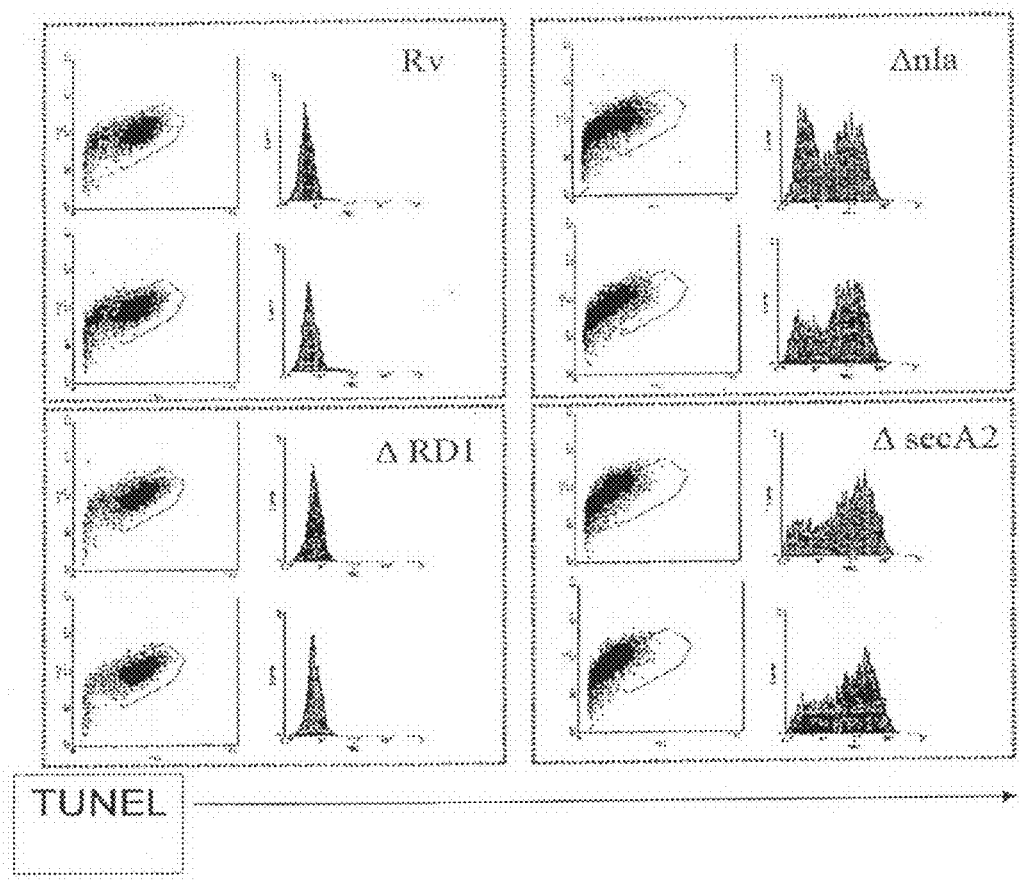
FIG. 2 is graphs of forward light scattering and TUNEL assays showing induction of apoptosis in THP-1 cells by *M. tuberculosis* ΔnlaA and ΔsecA2 cells.
Figure 3A:
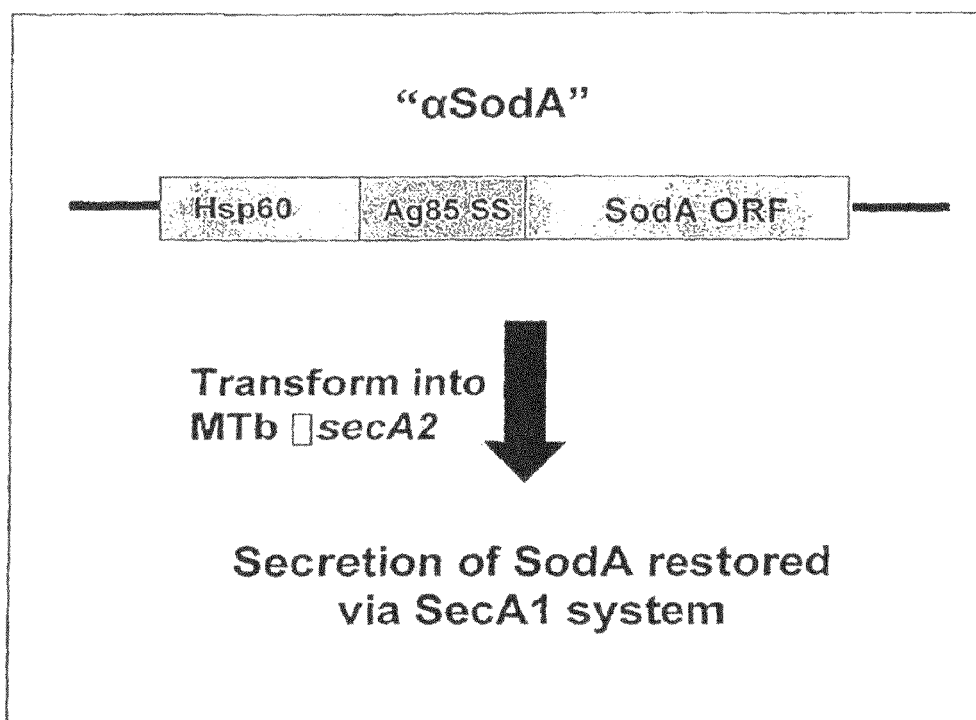
FIG. 3 is a diagram and graphs of TUNEL assays showing that restoring SodA secretion by a ΔsecA2 mutant reverses the effect of the secA2 deletion on host cell apoptosis. Panel A is a diagram of the strategy for restoring SodA secretion in a ΔsecA2 *M. tuberculosis* by expression of a transgenic SodA gene. Panel B is graphs of TUNEL assays showing induction of host cell apoptosis by ΔsecA2 *M. tuberculosis* but not by ΔseqA2-αSodA *M. tuberculosis*.
Figure 3B:
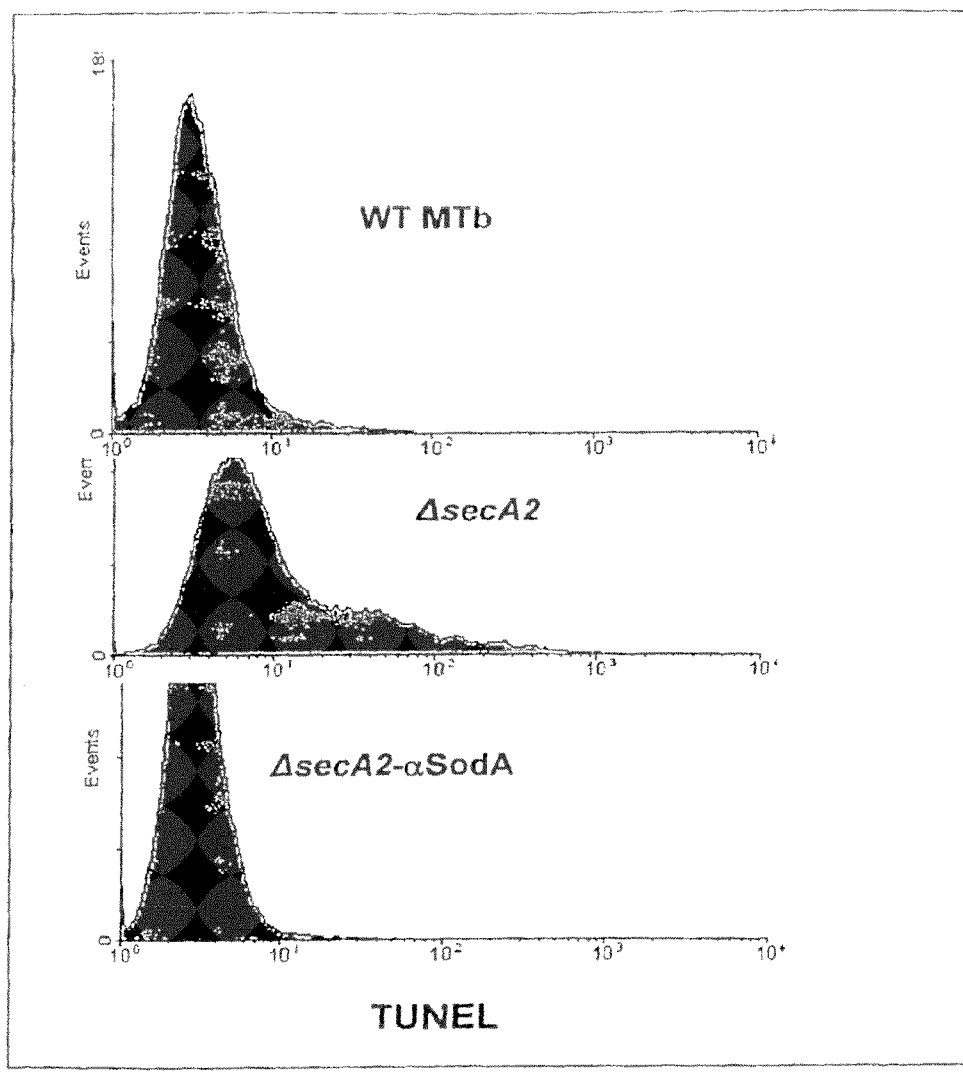
Figure 4:
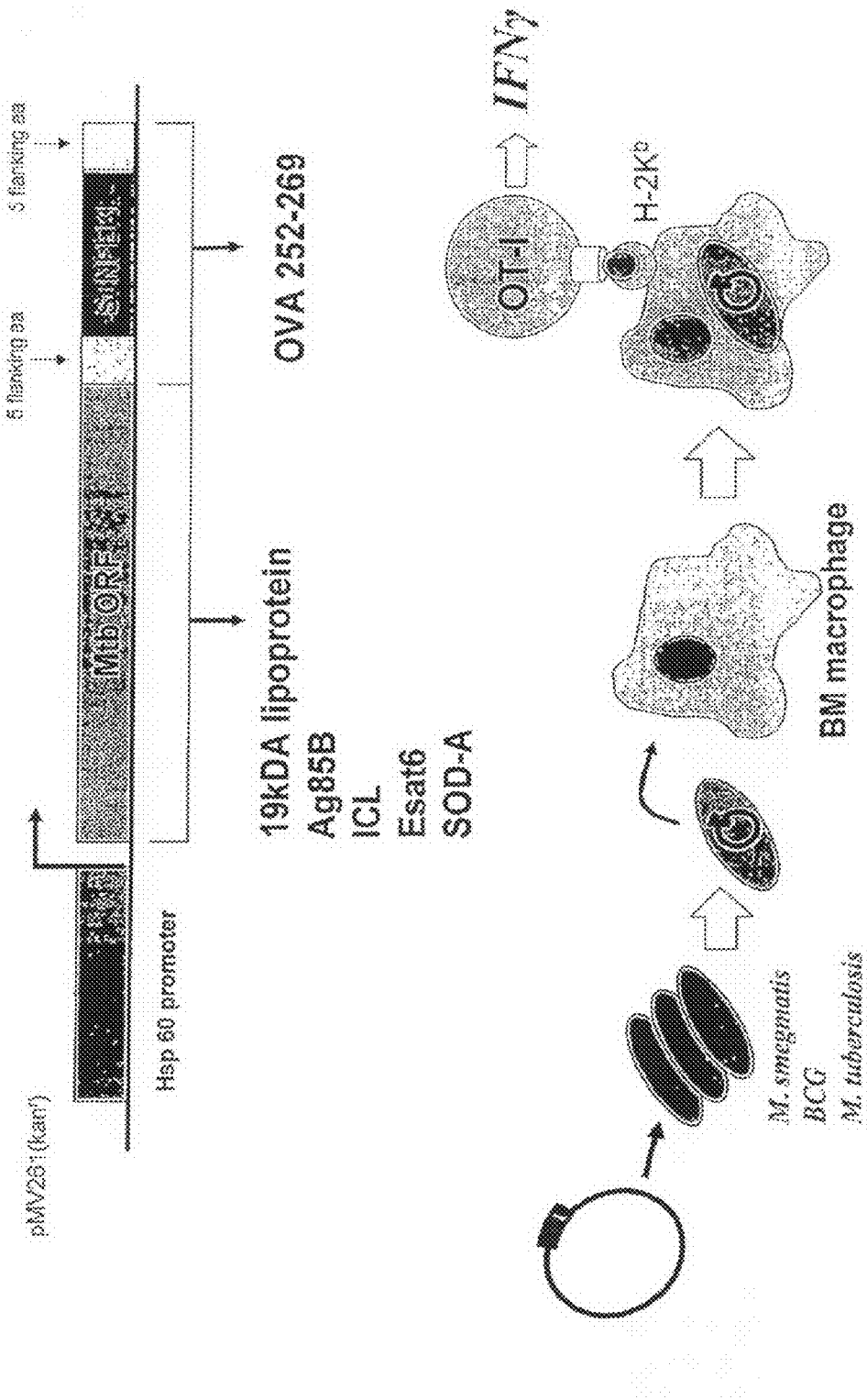
FIG. 4 is a diagram of the strategy used to evaluate the ability of various transgenic mycobacteria to induce interferon-γ (IFNγ) from OT-1 cells after exposure to macrophages. The mycobacteria are transfected with fusion proteins of *M. tuberculosis* antigens and the ovalbumin antigen SIINFEKL. Fusion proteins from transgenic mycobacteria that are apoptotic will be presented on the macrophage, where the SIINFEKL epitope will be recognized by the OT-1 cells, inducing IFNγ production by the OT-1 cells.
Figure 5:
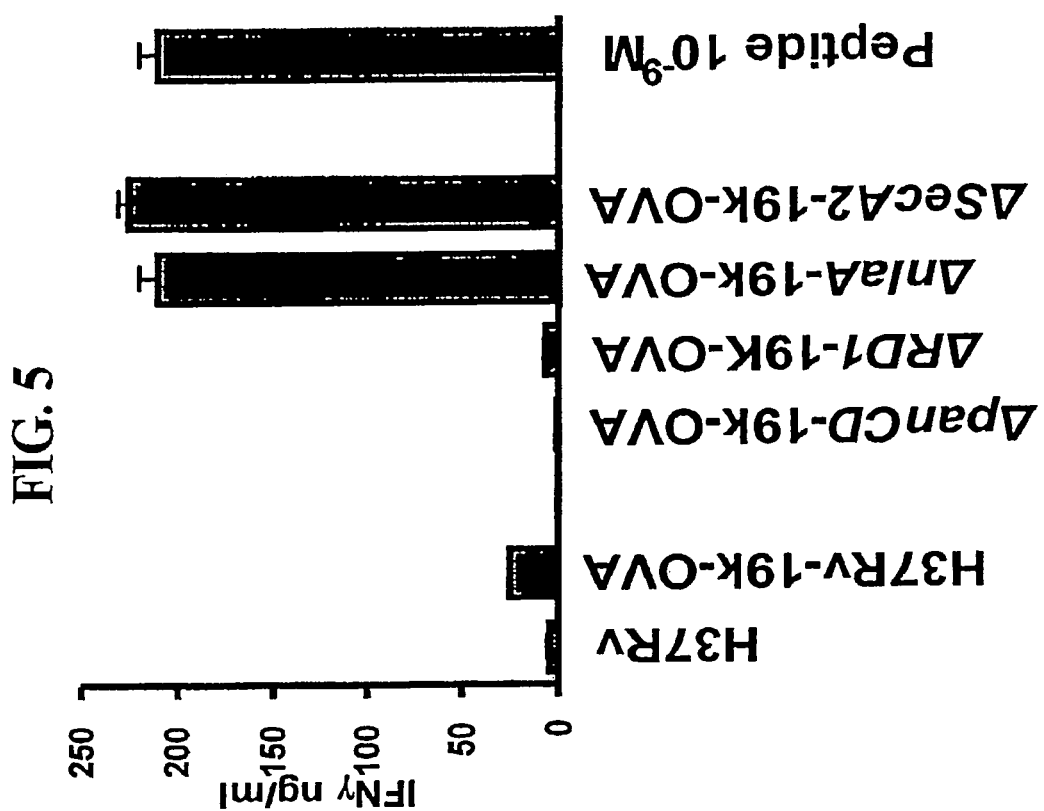
FIG. 5 is a graph of experimental data showing in vitro cross-presentation of the SIINFEKL peptide (OVA) by infected bone marrow-derived macrophages. The IFNγ production by the ΔnlaA-19k-OVA and ΔSecA2-19k-OVA indicates that the ΔnlaA and ΔSecA2 mutants are apoptotic.
Figure 6:
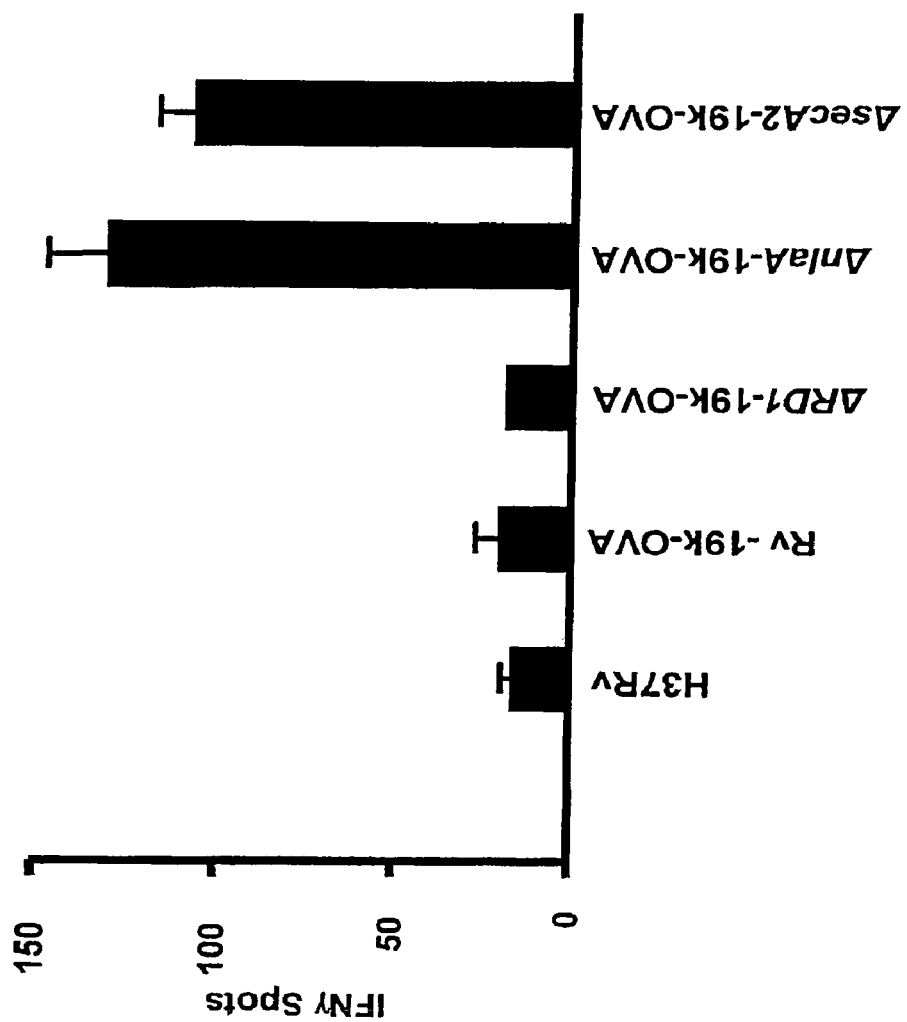
FIG. 6 is a graph of experimental data showing in vivo CD8 T cell priming by *M. tuberculosis* OVA (SIINFEKL)-expressing mutants with specific IFNγ ELISPOT analysis of splenocytes harvested on day 7 after i.v. mouse infection. The IFNγ production by the ΔnlaA-19k-OVA and ΔSecA2-19k-OVA indicates that the ΔnlaA and ΔSecA2 mutants are apoptotic.

Accordingly, the inventors have discovered that the SecA2 protein prevents host cell apoptosis. The inventors have also discovered that mycobacterial mutants that do not express SecA2 improve the ability of the mycobacterium to induce an immune response against virulent mycobacteria or recombinant antigens expressed by the mycobacteria.

Thus, the invention is directed to mycobacteria comprising (a) a mutation that is not in a SecA2 gene, where a wild-type mycobacterium comprising the mutation exhibits attenuated virulence in a mammal when compared with the wild-type mycobacterium without the mutation; and (b) a mutation in a SecA2 gene, wherein the mutation eliminates SecA2 activity.

These mycobacteria can be of any species, for example $M.$ $smegmatis,$ $M.$ $bovis,$ $M.$ $avium,$ $M.$ $phlei,$ $M.$ $fortuitum,$ $M.$ $lufu,$ $M.$ $paratuberculosis,$ $M.$ $habana,$ $M.$ $scrofulaceum,$ $M.$ $intracellulare,$ $M.$ $tuberculosis,$ or $M.$ $kansasi.$ Preferably, the mycobacterium is an $M.$ $bovis$ BCG or an $M.$ $tuberculosis,$ since those species are particularly useful as vaccines.

Since these mycobacteria are usually used in vivo, it is preferred that the mycobacteria is avirulent or rendered so, e.g., by selecting for avirulent strains or by engineering the mycobacteria to have a mutation or mutations that can fulfill that purpose. Many such mutations are known in the art, for example mutations that render the mycobacterium auxotrophic, e.g., a pan mutation or a Lys mutation, or mutations eliminating pathogenicity genes such as an RD1 deletion, as is known in the art. Thus, the mutation that is not in a SecA2 gene is preferably a deletion in at least a portion of an RD1 region, or a deletion in a gene controlling production of a vitamin or an amino acid. See, e.g., International Patent Publication No. WO 03/070164, incorporated herein by reference. It is also preferred that the mycobacterium utilized for this invention can colonize the host, in order for the mycobacterium to provide a long term antigenic stimulus to the host, thus establishing a strong immune response.

Although these mycobacteria can be produced using non-recombinant methods, e.g., using mutagens and selection for the ΔsecA2 phenotype, it is preferred that at least one of the mutations was made by genetic engineering methods, since those methods are much easier and more accurate than non-recombinant methods.

The mycobacterium can optionally further comprise a recombinant gene operably linked to a promoter that directs expression of the gene when the mycobacterium infects a mammalian cell. Preferably, the gene encodes an antigen, for example of a neoplasm, tumor or cancer, or most preferably an antigen of a human pathogen, to take advantage of the increased immunogenicity to the antigen as a result of the ΔSecA2 mutation. Examples of pathogens (e.g., human pathogens) where antigens useful in these mycobacteria include viruses (e.g., HIV, hepatitis C virus, herpes virus, influenza, smallpox, diphtheria, tetanus, measles, mumps, rabies, poliovirus etc), bacteria (e.g., pathogenic mycobacteria, $Salmonella$ sp., etc.), and eukaryotic parasites (e.g., malaria, $Leishmania,$ etc.).

The invention is also directed to mycobacteria comprising a mutation in a SecA2 gene. where the mutation eliminates SecA2 activity. These mycobacteria are not $Mycobacterium$ $tuberculosis$ or $Mycobacterium$ $smegmatis.$ However, they may be of any other mycobacterial species. Preferably, the mycobacterium is a $Mycobacterium$ $bovis,$ most preferably $Mycobacterium$ $bovis$ BCG. As with the mycobacteria described above, the mutation of these mycobacteria was preferably made by genetic engineering methods. Also as with the mycobacteria described above, these mycobacteria can further comprise a recombinant gene operably linked to a promoter that directs expression of the gene when the mycobacterium infects a mammalian cell. Preferably, the gene encodes an antigen, for example of a neoplasm, tumor or cancer, or most preferably an antigen of a human pathogen. Examples of pathogens (e.g., human pathogens) where antigens useful in these mycobacteria include viruses, bacteria, and eukaryotic parasites.

The present invention is additionally directed to methods of inducing an immune response in a mammal. The methods comprise inoculating the mammal with any of the above-described mycobacteria.

The invention is also directed to methods of inducing an immune response to a pathogenic mycobacterium in a human.

The methods comprise inoculating the human with a mycobacterium vaccine. The mycobacterium vaccine comprises a mycobacterium comprising a mutation in a SecA2 gene, where the mutation eliminates SecA2 activity. Preferably, the mycobacterium vaccine comprises an *M. bovis* or an *M. tuberculosis*, most preferably an *M. bovis* BCG.

The mycobacterium in the mycobacterium vaccine can also further comprise a mutation that is not in a SecA2 gene, where a wild-type mycobacterium comprising the mutation that is not in a SecA2 gene exhibits attenuated virulence in a mammal when compared with the wild-type mycobacterium without the mutation that is not in a SecA2 gene. These mutations are generally important when the wild-type mycobacterium that the vaccine was derived from is a virulent pathogen, for example *M. tuberculosis*. Preferably, the mutation that is not in a SecA2 gene is a deletion in at least a portion of an RD1 region, or a deletion in a gene controlling production of a vitamin or an amino acid.

As with the mycobacteria discussed above, the mycobacterium in the mycobacterium vaccine can optionally further comprise a recombinant gene operably linked to a promoter that directs expression of the gene when the mycobacterium infects a mammalian cell. Preferably, the gene encodes an antigen, for example of a neoplasm, tumor or cancer, or most preferably an antigen of a human pathogen, to take advantage of the increased immunogenicity to the antigen as a result of the ΔSecA2 mutation. Examples of pathogens (e.g., human pathogens) where antigens useful in these mycobacteria include viruses, bacteria, and eukaryotic parasites.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE 1

Immunological Evaluation of ΔnlaA and ΔSecA2 Mutants

The ability of ΔnlaA (SEQ ID NO:11-nlaA amino acid sequence MKRYLTIIYGAASYLVFLVAFGYAIG-FVGDVVVPRTVDHAIAAPIGQAVVVNLVLLGVF AVQHSVMARQGFKRWWTRFVPPSIERSTYVLLAS-VALLLLYWQWRTMPAVIWDVRQP AGRVALWALF-WLGWATVLTSTFMINHFELFGLRQVYLAWRGKP-YTEIGFQAHLLYRW VRHPIMLGFVVAFWATPM-MTAGHLLFAIGATGYILVALQFEERDLLAALGD-QYRDYRR EVSMLLPWPHRHT SEQ ID NO:12-nlaA cDNA sequence atgaagcgttatttgacgatcatt-tacgggggccgcgagctatctgg- tattcctggttgccttcgggtatgc-gatcggtttcgtcggcgacgtagt ggtgccacgaaccgtagatcacgc-gatcgcggcgccgatcggccaggcggtcgtggtcaacttggtgctgctgggcgt-gttcgccgtcca acatagcgtgatggcacga-cagggtttcaaacgctggtggactcgat-tcgtgccgccctcgatcgagcgcagcacctatgtactgctggcc agcgttgcgct-gttgttgctgtactggcaatggcgaacgatgccggcggtcatctgggacgtgcgg-cagccggctggccgggtggcgttg tgggcgttgttctggctcgggtgggc-cacggtgttgacgtcgactttcatgat-caatcatttcgaattgttcggcctacggcaggtgtatttggc ttggcgcggaaagc-cgtacaccgagatcggttttcaggctcatctgctctaccggtgggtacgccacccga tcatgctcggattcgtcgtcg cgttctgggcgacgcccatgatgacg-gcggggcacttgcttttcgcgatcggcgcgacgggctacatcttggtcgcgttg-cagttcgaaga gcgcgacctactcgcggcgctgggcgac-caataccgcgattaccgccgcgaggtgtcgatgt-tgttgccgtggccgcaccggcatacctg a) and ΔsecA2 mutants (Braunstein et al., 2003) to induce host apoptosis and immunity to mycobacteria was evaluated using immunological and flow cytometric methods.

THP-1 cells (human myeloid/monocytic cell line) were infected with *M. tuberculosis* strains H37Rv, ΔRD1 (Hsu T, et al., 2003), ΔnlaA and ΔsecA2 at an MOI of 10:1. The cells were harvested after 60 hours, and analyzed by TUNEL as follows. The cells were stained with the In Situ Cell Death Kit (Roche), which labels strand breaks by the terminal deoxynucleotidyl transferase-mediated addition of fluorescein dUTP to free 3'-OH DNA ends. The size and complexity of the infected THP-1 cells was assessed by measurement of forward and side light scattering, and DNA fragmentation was assayed by determination of fluorescein incorporation using fluorescence-activated cell sorter (FACS) (Schrijvers et al., 2004) THP-1 cells infected with ΔnlaA or ΔsecA2, but not Rv or ΔRD1, showed extensive apoptosis (FIGS. 1 and 2).

The *M. tuberculosis*-SecA2 gene functions in superoxide dismutase A (SodA) secretion (Braunstein et al., 2003). Deleting SecA2 from virulent *M. tuberculosis* attenuates the virulence of the mycobacterium in mice. To evaluate whether the SecA2 superoxide dismutase prevents apoptosis, SodA activity was restored by transfecting an *M. tuberculosis* ΔsecA2 mutant with an αSodA plasmid construct (FIG. 3A). That vector features an Hsp60 promoter and an Ag85 signal sequence driving expression of a SodA gene (Braunstein et al., 2000). This plasmid drives the constitutive expression of a SodA protein that is secreted by the SecA1 system. This provides a SodA protein that is not dependent on SecA2 and thus complements the defective secretion of SodA from the ΔSecA2 mutant. THP-1 cells were infected with the wild type *M. tuberculosis* H37Rv, the ΔSecA2 mutant, and the ΔSecA2-αSodA SOD restored strain and the extent of apoptosis of the THP-1 cells was evaluated using TUNEL as described above. As shown in FIG. 28B, the ΔSecA2 mutant induced apoptosis, but the ΔSecA2-αSodA strain restored the ability of the mycobacterium to inhibit apoptosis. This indicates that the secretion of SodA protein can be directly responsible for inhibition of infection-induced apoptosis.

Apoptosis is believed to function in host defense by making pathogen antigens available for presentation by bystander dendritic cells (Schaible et al., 2003; Yrlid and Wick, 2000). To determine if macrophages present more pathogen antigens when infected with mycobacteria that induce apoptosis than when infected with mycobacteria that do not induce apoptosis, the apoptosis-inducing mycobacterial strains ΔsecA2 and ΔnlaA, and the apoptosis-suppressing strains H37Rv (virulent), ΔRD1 and ΔpanCD (attenuated virulence—see International Patent Publication No. WO 03/070164, incorporated herein by reference) were transfected with plasmid constructs comprising the 19 kDA lipoprotein antigen fused to the coding sequence for amino acid residues 252-269 (SIINFEKL [SEQ ID NO: 1]) of chicken ovalbumin (OVA) under the control of the Hsp 60 promoter (FIG. 4), creating ΔsecA2-19k-OVA, ΔnlaA-19k-OVA, H37Rv-19k-OVA, ΔRD1-19k-OVA and ΔpanCD-19k-OVA. Each of these strains was combined with bone marrow-derived macrophages to allow infection of the macrophages, then T cells from TCR transgenic OT-1 mice (SINFEKL/H-2 $K^b$ specific) were added and interferon-γ (IFNγ) was measured by ELISA. The OVA peptide antigen is presented on the MHC Class I H-2 $K^b$ molecule on the macrophages, where the OVA antigen is recognized by the T cell receptor on OT-1 cells, causing production of IFNγ (FIG. 4). As shown in FIG. 5, only the strains that allow host apoptosis, ΔsecA2-19k-OVA and ΔnlaA-19k-OVA, stimulated OT-1 production of IFNγ.

Figure 7:
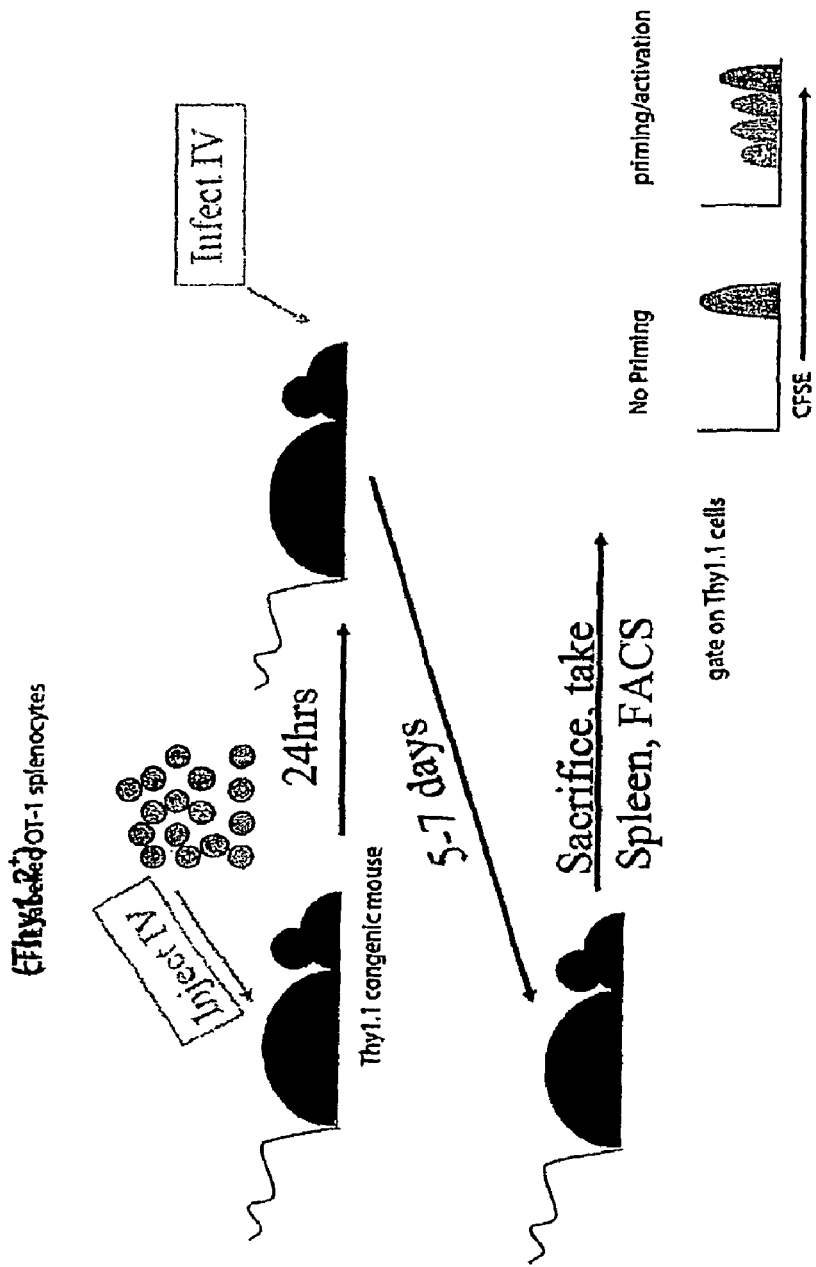
FIG. 7 is a diagram showing the strategy for determining the effect of infection with a mycobacterium on proliferation of carboxy-fluorescein diacetate, succinimidyl ester (CFSE)-labeled OT-1 splenocytes.
Figure 8:
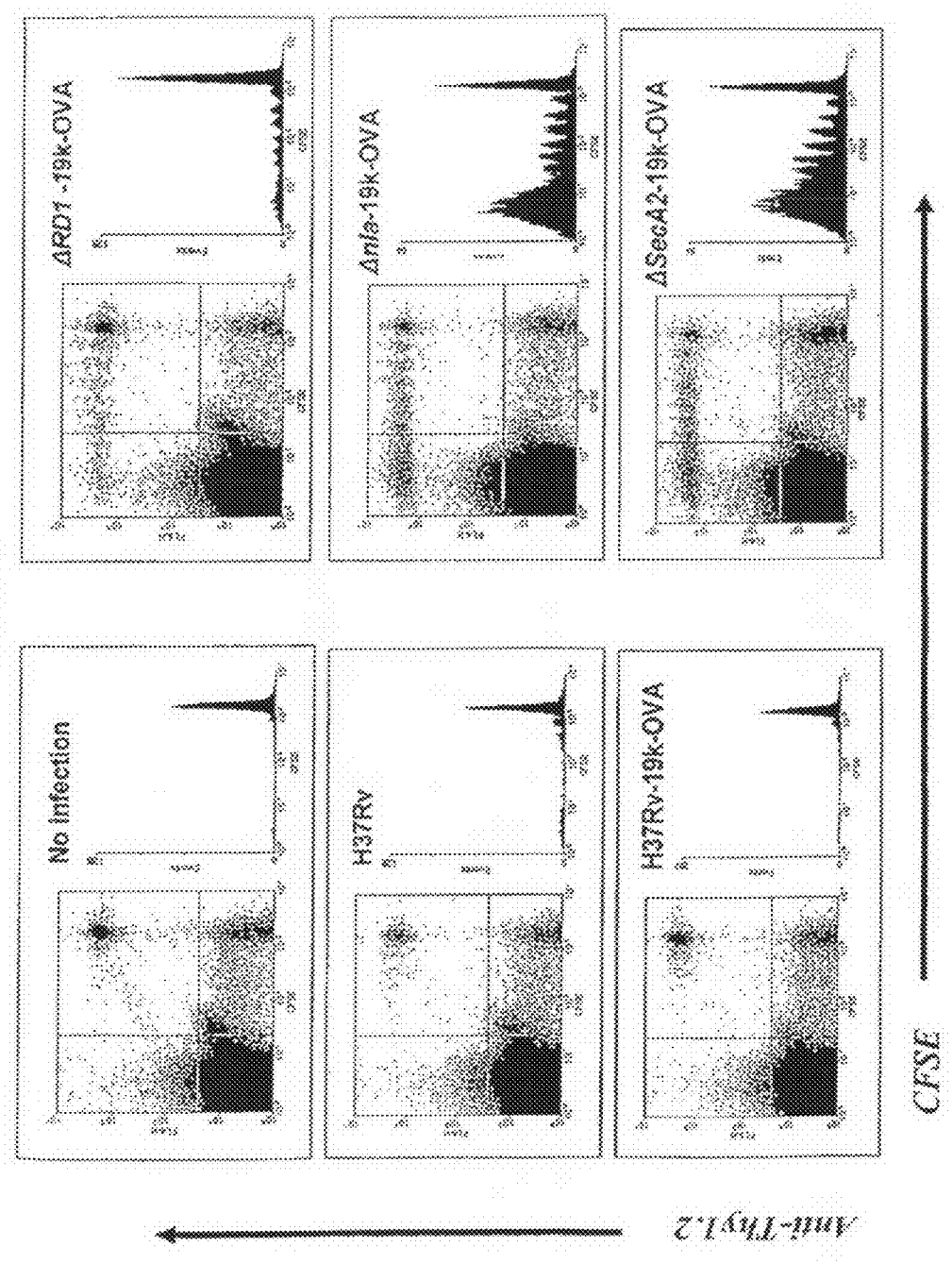
FIG. 8 is graphs of experimental results showing the activation of naïve CD8+ T cells by apoptosis-inducing *M. tuberculosis* mutants ΔnlaA-19k-OVA and ΔSecA2-19k-OVA.

The ability of the above-described mutants expressing the transgenic 19k-OVA fusion protein to stimulate splenocyte proliferation in vivo was determined by injecting OT-1 splenocytes (Thy 1.2+) labeled with 5(6)-carboxyfluorescein diacetate N-succinimidyl ester (CFSE) into Thy1.1 congenic mice then, after 24 hours, infecting the mice with the mutant mycobacterium. After 5-7 days, the mice were sacrificed and their splenocytes were analyzed by FACS to determine the intensity of CFSE fluorescence in the Thy 1.2$^+$ T cells (FIG. 7). The CFSE enters the cells and binds irreversibly to intracellular and cell surface proteins by reaction with amines. When cells divide, the fluorescence intensity of each daughter cell is halved, so a proliferating cell population (e.g., antigen-activated T cells) exhibits a flow cytometry fluorescence profile as shown at the bottom right of FIG. 7. Results of these experiments are shown in FIG. 8. Only the strains that allow host apoptosis, ΔsecA2-19k-OVA and ΔnlaA-19k-OVA, exhibited OT-1 T cell activation in vivo. This indicates that apoptosis of infected cells promotes priming and activation of T cells against mycobacterial antigens.

Figure 9:
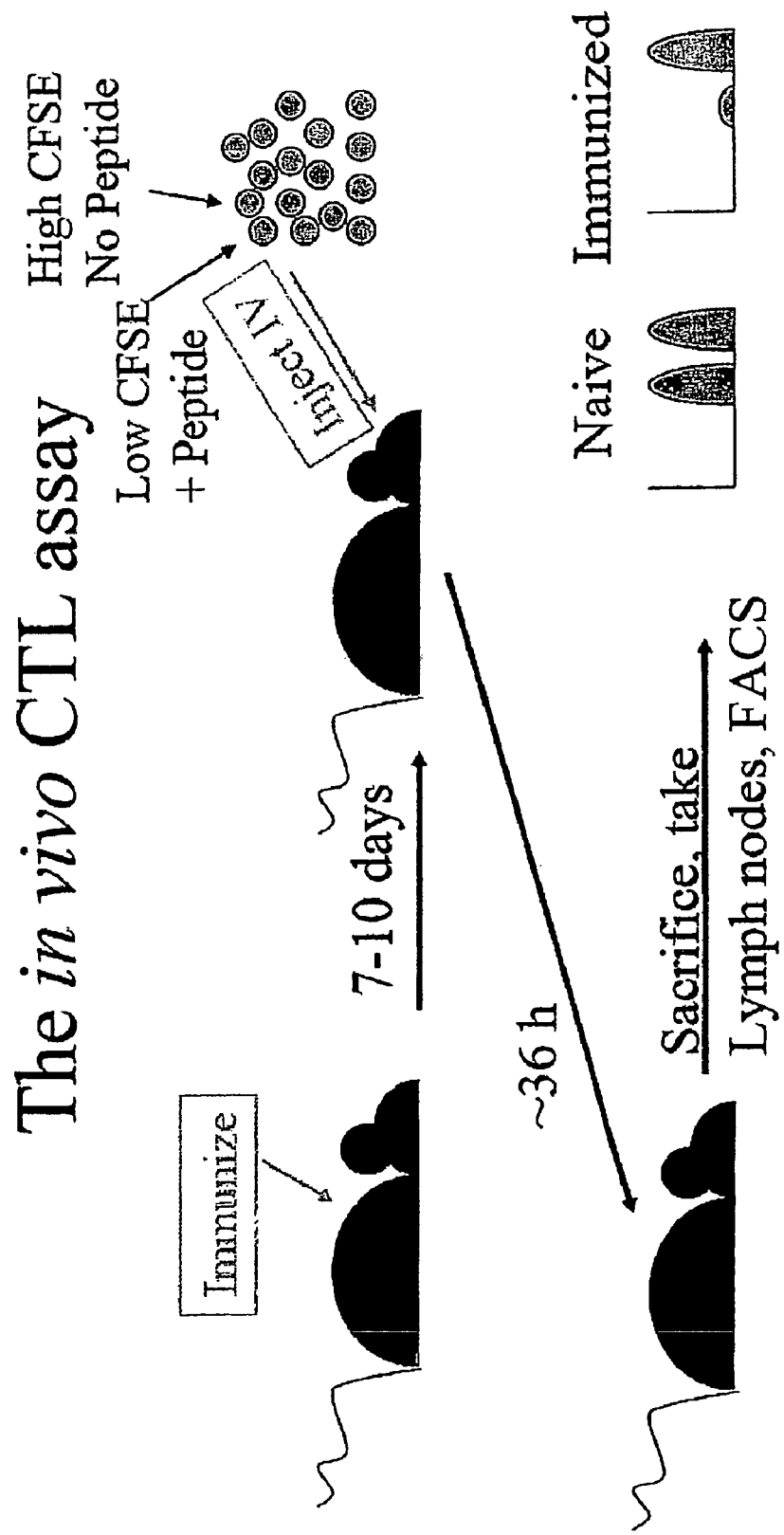
FIG. 9 is a diagram showing the strategy for determining the ability of a mycobacterium to induce a CTL immune response in vivo.

The ability of the apoptosis-inducing mutants to induce an immune response to mycobacterial antigens was further evaluated with the in vivo cytotoxic T lymphocyte (CTL) assay outlined in FIG. 9. Mice were immunized with the 19k-OVA antigen mycobacterial strains described above. After 7-10 days, the mice were then injected with $10^7$ Thy1.2$^+$T cells that were either labeled with (a) a low concentration of CFSE and the OVA SIINFEKL peptide, or (b) a high concentration of CFSE without the OVA peptide. About 36 h later, the mice were sacrificed and FACS analysis was performed to quantify low and high-intensity fluorescing lymph node cells. Where the mouse has a CTL response specific for the OVA peptide, that response would kill only the CFSE$^{lo}$ cells; the CFSE$^{hi}$ cells should be unaffected and serve as a control.

Figure 10:
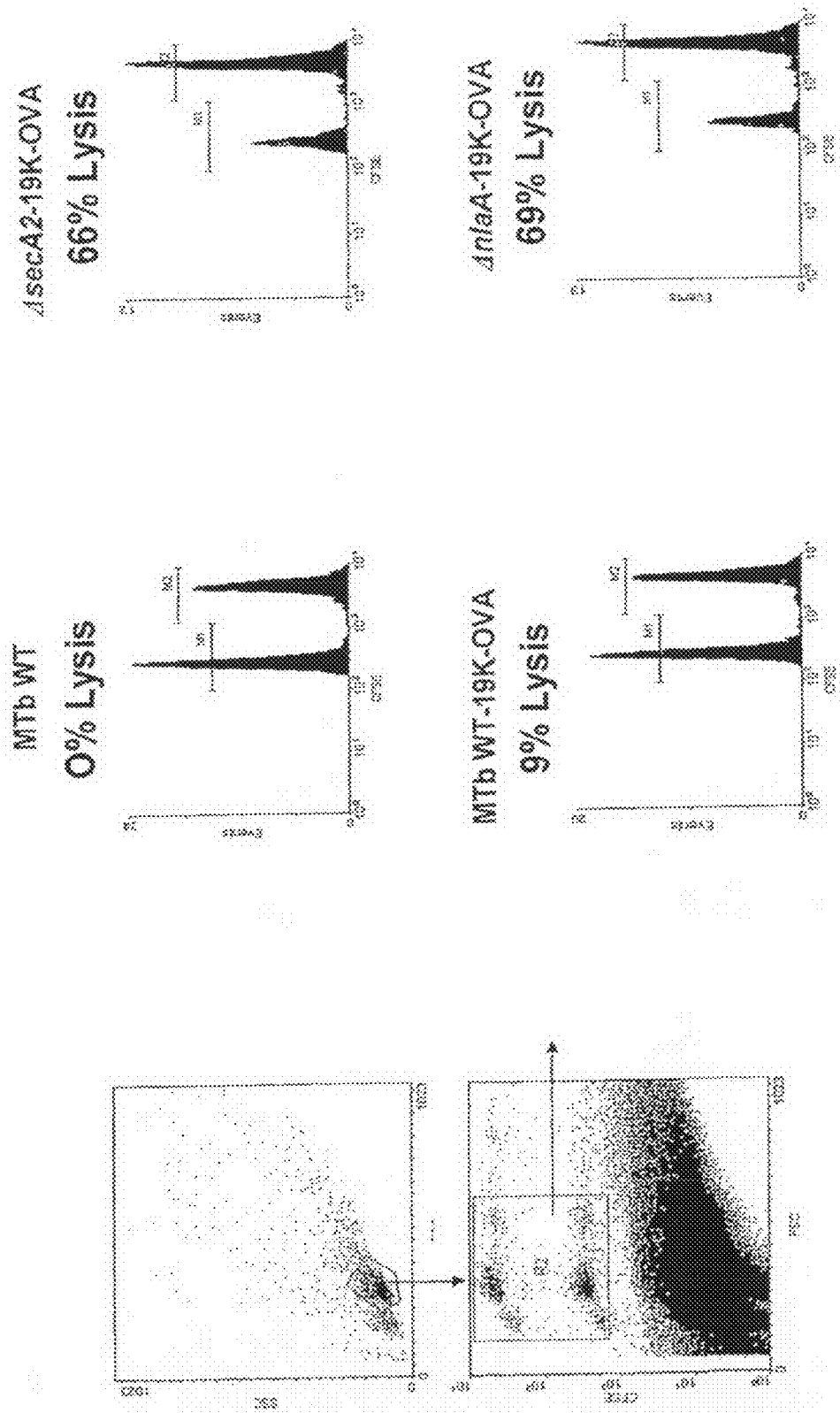
FIG. 10 is graphs of experimental results showing that *M. tuberculosis* mutants ΔnlaA-19k-OVA and ΔSecA2-19k-OVA induces a CTL response to cells presenting the 19k-OVA antigen.

FIG. 10 shows results of that assay. The mice immunized with the apoptosis-inducing mycobacteria mounted a CTL response to the OVA antigen-bearing T cells, whereas the mice immunized with the analogous mycobacteria that did not induce apoptosis did not mount the CTL response.

EXAMPLE 2

Inoculation with *Mycobacterium tuberculosis* Mutants that Inhibit Host Apoptosis Attenuates Infection with Virulent *Mycobacterium tuberculosis*

Mice were vaccinated with 106 organisms of *M. bovis* BCG, the transgenic *M. tuberculosis* with the nlaA deletion described in Example 1 (ΔnlaA in Table 1), a transgenic *M. tuberculosis* combining the ΔsecA2 and ΔnlA deletions described above (ΔsecA2/ΔnlaA), and a transgenic *M. tuberculosis* having deletions in RD1 and pan, as described in International Patent Publication No. WO 03/070164 A2, incorporated herewith by reference, and expressing a transgenic listeriolysin (as in Grode et al., 2005)(ΔRD1/Δpan-listeriolysin). Two months following vaccination, the mice were challenged with 200 CFUs of *M. tuberculosis* Erdman by aerosol route. TB growth in the lungs and spleens were evaluated at 1 month and 3 months post-challenge. Results are provided in Table 1.

TABLE 1

| Values are in $\log_{10}$. | Lungs | Spleens |
|---|---|---|
| 1 month: | | |
| Naive | 6.30 ± 0.06 | 5.35 ± 0.07 |
| BCG | 4.92 ± 0.07 (−1.38) | 4.24 ± 0.18 (−1.11) |
| ΔnlaA | 4.52 ± 0.15 (−1.78) | 4.04 ± 0.24 (−1.31) |
| ΔsecA2/ΔnlaA | 5.25 ± 0.08 (−1.05) | 4.27 ± 0.20 (−1.08) |
| 3 months: | | |
| Naive | 5.43 ± 0.02 | 4.93 ± 0.10 |
| BCG | 4.92 ± 0.14 (−0.51) | 4.31 ± 0.11 (−0.62) |
| ΔnlaA | 4.56 ± 0.16 (−0.87) | 3.79 ± 0.26 (−1.14) |
| ΔsecA2/ΔnlaA | 5.17 ± 0.14 (−0.26) | 4.88 ± 0.09 (−0.05) |

In a second experiment using the same protocol, protection with *M. tuberculosis* ΔsecA2 and ΔnlaA, along with BCG, was evaluated (Table 2).

TABLE 2

| Group | 1 mo. lung | 1 mo. spleen | 3 mo. lung | 3 mo. spleen |
|---|---|---|---|---|
| naive | 6.67 ± 0.08 | 4.61 ± 0.04 | 5.78 ± 0.02 | 4.79 ± 0.03 |
| ΔsecA2 | 4.77 ± 0.07 (−1.90) | 3.84 ± 0.11 (−0.77) | 5.16 ± 0.05 (−0.62) | 4.49 ± 0.15 |
| ΔnlaA | 5.34 ± 0.08 (−1.33) | 4.04 ± 0.19 (−0.57) | 5.38 ± 0.09 (−0.40) | 4.67 ± 0.07 |
| BCG | 5.52 ± 0.02 (−1.15) | 3.76 ± 0.08 (−0.85) | 5.73 ± 0.14 | 4.67 ± 0.09 |

Cytokine induction by BCG, the ΔnlaA mutant, and the ΔsecA2/ΔnlaA mutant was also determined. Two months after vaccination with 106 organisms, mice were challenged with 200 CFUs of *M. tuberculosis* Erdman by aerosol route. At 10 days post-challenge, lung cells were removed and analyzed for cytokine message using real-time PCR (cells directly without in vitro stimulation). The results are reported in Table 3 as message levels relative to the GAPDH housekeeping gene.

TABLE 3

| Expt. Group | IFN-γ | IL-12 | IL-4 |
|---|---|---|---|
| Naive | 4.0 | 30 | 0.8 |
| BCG | 27 | 25 | 0.3 |
| ΔnlaA | 32 | 16 | 0.3 |
| ΔsecA2/ΔnlaA | 39 | 20 | 1.3 |

EXAMPLE 3

Further Characterization of SecA2 Mutants

A mutant of *Mycobacterium tuberculosis* containing an in-frame complete deletion of the secA2 gene, $mc^2 3112$, is attenuated in its virulence in the murine model of tuberculosis (Braunstein et al., 2003). SecA2 is an accessory secretion factor that is required for the export of a subset of *M. tuberculosis* proteins into the culture filtrate (Braunstein et al., 2003). One of the proteins that is dependent on SecA2 is the antioxidant superoxide dismutase A (SodA). Edwards et al. reported that a SodA diminished *M. tuberculosis* strain is attenuated in virulence and that there is increased apoptotic cells in the lungs of mice infected with the SodA-attenuated *M. tuberculosis* strain (Edwards et al., 2001). Examples 1 and 2 above show that the secA2 mutant leads to increased apoptosis in the host and promotes antigen presentation and T cell activation. This is consistent with Schaible et al. (2003) who reported that *M. tuberculosis* induced apoptosis serves to promote antigen presentation by way of apoptotic vesicles carrying MTB antigens to uninfected antigen presenting cells. This suggests that increased apoptosis could facilitate development of a protective immune response to *M. tuberculosis* infection.

The incorporation of pro-apoptotic properties into mycobacterial vaccines, including *M. tuberculosis* vaccines and M bovis BCG vaccines, could greatly benefit the protective response elicited. Consequently, the secA2 mutant of *M. tuberculosis* and a secA2 mutant of *M. bovis* BCG are candidates for improved live mycobacteria vaccines. A secA2 mutant strain of *M. bovis* BCG was therefore constructed.

Construction of a *M. bovis* BCG mutant with an in-frame deletion of the secA2 gene. An allelic exchange strategy involving a suicide counterselectable vector, pMB179, was used to create the mutant (Braunstein et al., 2003). *M. bovis* BCG Pasteur (W. R. Jacobs' strain collection) and *M. bovis* BCG Tice (Oranon) was electroporated with 1 μg of base treated pMB179 plasmid DNA. Suicide vector pMB179 contains a secA2 deletion allele as well as a counterselectable sacB marker and selectable hyg (hygromycin resistance) marker. A hygromycin resistant colony arising from a single-crossover event between the deleted secA2 allele on pMB179 and secA2 in the chromosome was obtained from each strain. These single-crossover strains, *M. bovis* BCG Pasteur MB542 and *M. bovis* BCG Tice MB543, contain mutated and wild-type secA2 alleles separated by the vector hyg and sacB sequences. MB542 and MB543 were each grown to saturation and 0.5 ml was used to inoculate 10 ml of 7H9-ADS medium. Following 10 days growth, serial dilutions were plated onto 7H10-ADS agar with 3% sucrose. The expression of sacB in mycobacteria prevents growth on sucrose medium. Sucrose resistant and hygromycin sensitive recombinants arising from a second recombination event between the two alleles of secA2 were obtained. Genomic DNA was isolated from the recombinants and Southern analysis was performed to identify the secA2 allele present. DNA digested with EcoRI/HindIII was probed with a 1.5 kb EcoRI/HindIII fragment of plasmid pMB146. The following secA2 mutants were obtained: MB544 is a secA2 mutant of *M. bovis* BCG Pasteur and MB546 is a secA2 mutant of *M. bovis* BCG Tice. The resulting deletion mutant is an in-frame unmarked mutation of secA2 with the majority of the secA2 gene deleted. Full length SecA2 is 808 amino acids in length while the secA2 deletion mutation encodes for only the first 31 amino acids in-frame with the last 49 amino acids of SecA2. The secA2 deletion in both of these BCG mutants is identical to that in the corresponding *M. tuberculosis* mutant.

Figure 11:
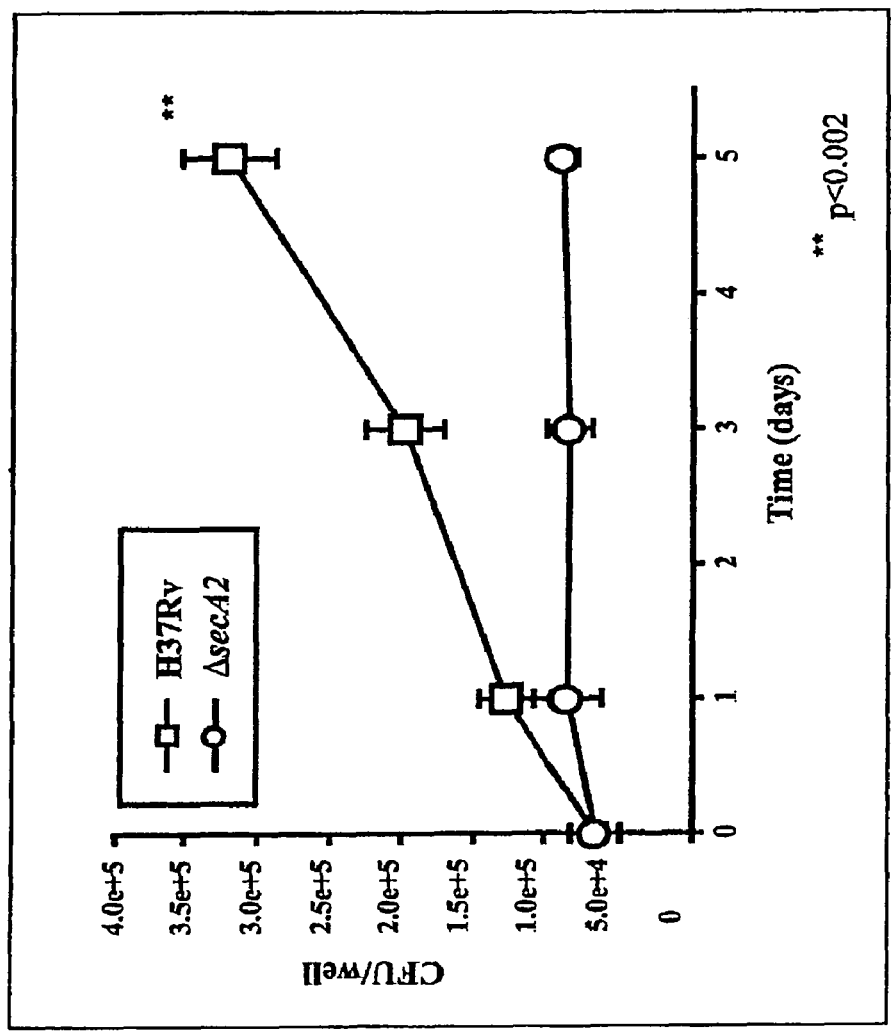
FIG. 11 is a graph of experimental results showing that the secA2 mutant is defective for growth in murine bone marrow macrophages. Bone marrow derived macrophages were obtained from C57BL/6 mice, 2×10$^5$ macrophages were plated into wells on chamber slides, and the macrophages were then infected for 4 hrs with, *M. tuberculosis* at a multiplicity of infection (MOI) of 1.0. After 4 hrs, the macrophage monolayers were washed and fresh media added. CFUs were determined by lysing the monolayers and plating serial dilutions of the lysates. The strains shown are H37Rv (squares) and secA2 mutant (circles). The graph represents ±SEM of 8 independent experiments.

Elucidating the role of *M. tuberculosis* SecA2 in macrophages. The attenuated phenotype reported previously for the *M. tuberculosis* secA2 mutant in mice was a defect in growth during the early phase of infection (Braunstein et al., 2003). During this growth-in vivo period of infection *M. tuberculosis* is replicating in macrophages. This suggested that the secA2 mutant is defective for growth in macrophages. To test this hypothesis murine bone marrow derived macrophages from C57BL/6 mice were infected with H37Rv or the secA2 mutant and the number of viable bacteria associated with the macrophages over time was determined by plating macrophage lysates. These experiments have demonstrated that the secA2 mutant, in comparison to H37Rv, is defective in its ability to grow within these macrophages (FIG. 11). These results are consistent with the observed growth-in vivo defect of the *M. tuberculosis* secA2 mutant.

*M. tuberculosis* suppresses the immune response of the host which could be important to pathogenesis and the development of a protective immune response (Beltan et al., 2000; Hussain et al., 1999; Nau et al., 2002; Noss et al., 2000). This example shows that IFN-γ treated cells that are infected with the *M. tuberculosis* secA2 mutant are more highly activated than the corresponding cells infected with the wild-type *M. tuberculosis* H37Rv strain. This suggests a role for SecA2 in the inhibition of macrophage activation, which could account for its role in virulence. It also suggests that immunization with a secA2 mutant of *M. tuberculosis* or *M. bovis* BCG may elicit a stronger immune response through increased host cell activation.

Figure 12:
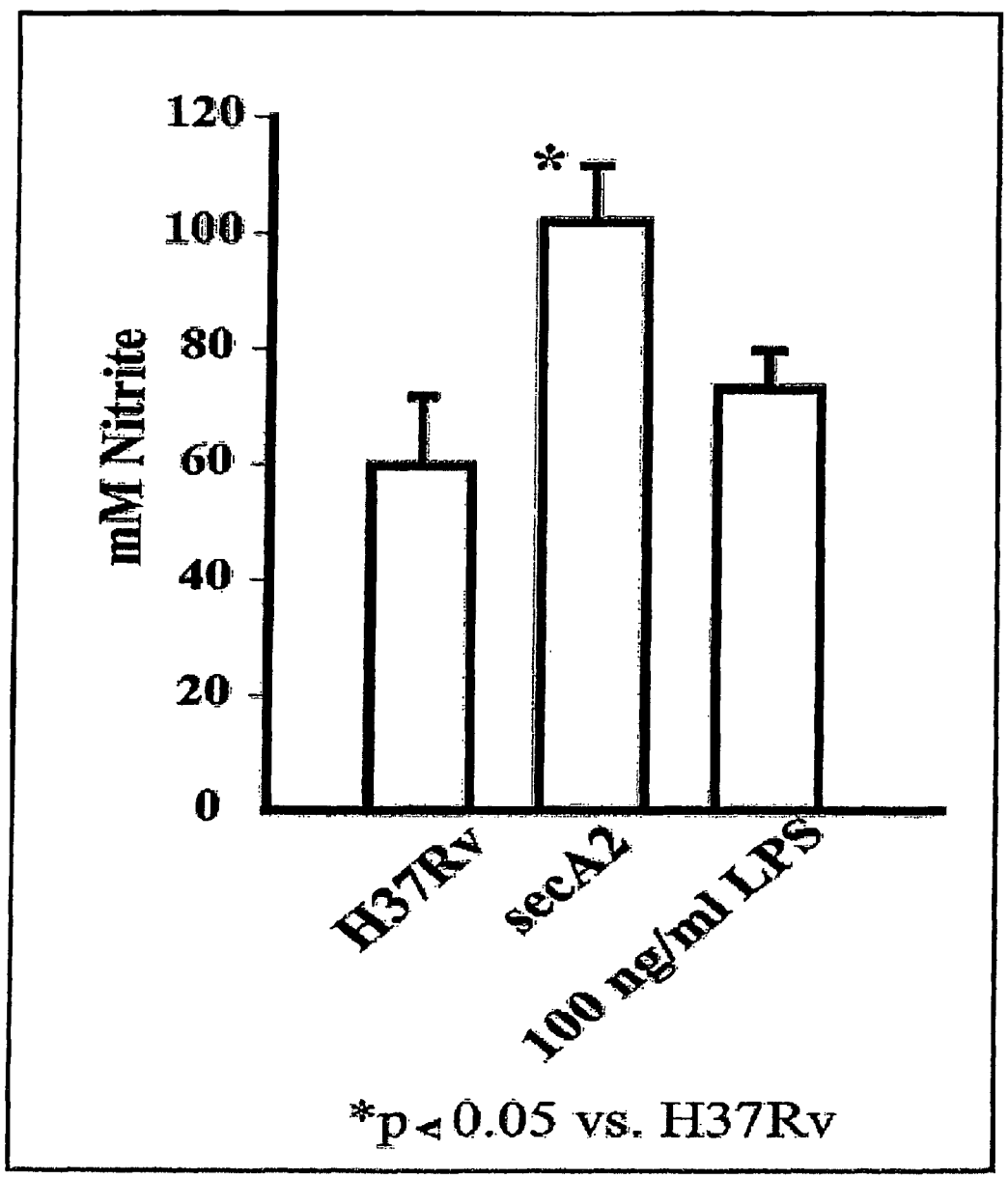
FIG. 12 is a graph of experimental results showing that the secA2 mutant elicits more Reactive Nitrogen Intermediates (RNI) from INF-γ treated macrophages. Bone marrow derived macrophages from C57BL/6 mice were activated by pretreatment for 24 hrs with 100 U/ml murine INF-γ. The macrophages were infected at an MOI of 10. INF-γ was maintained throughout the 4 hr bacterial uptake period. Following uptake, monolayers were washed and fresh media was added. RNI was measured 24 hours after infection using the Griess reagent. Graph represents the average±SEM of 5 experiments.
Figure 13:
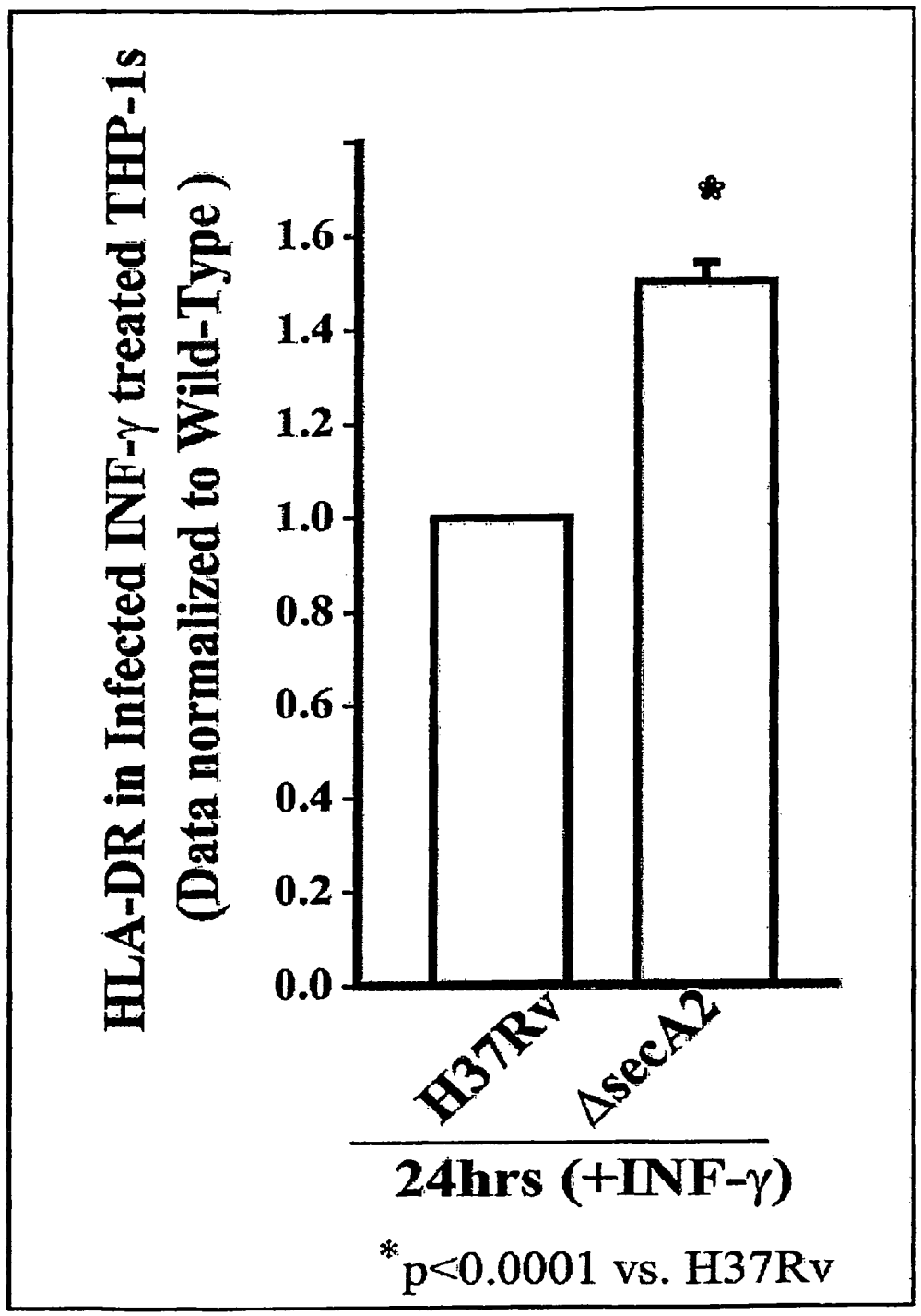
FIG. 13 is a graph of experimental results showing that the secA2 mutant elicits more HLA-DR message from INF-γ treated THP-1 cells. PMA differentiated THP-1 cells were infected at an MOI of 10 in the presence of human INF-γ for 24 hours. Total RNA was isolated from infected cells using TRIzol. HLA-DR expression was determined by quantitative real-time RT-PCR. HLA-DR expression was normalized to expression of 18S ribosomal RNA. Graph represents the average±SEM of 4 experiments.

As shown in FIGS. 12 and 13, cultured cells treated with IFN-γ and infected with the secA2 *M. tuberculosis* mutant were more activated (on the basis of increased production of Reactive Nitrogen Intermediates and HLA-DR/MHC Class II message) than the same cells infected with H37Rv.

EXAMPLE 4

The SecA2 Secretion Factor of *Mycobacterium tuberculosis* Promotes Growth in Macrophages and Inhibits the Host Immune Response Example Summary The SecA protein is present in all bacteria, and it is a central component of the general Sec-dependent protein export pathway. An unusual property of *Mycobacterium tuberculosis* is the presence of two SecA proteins: SecA1, the essential "housekeeping" SecA, and SecA2; the accessory secretion factor. Here we report that a ΔsecA2 mutant of *M. tuberculosis* was defective for growth in the early stages of low dose aerosol infection of C57BL/6 mice, a time during which the *bacillus* is primarily replicating in macrophages. Consistent with this in vivo phenotype, we found that the ΔsecA2 mutant was defective for growth in macrophages from C57BL/6 mice. The ΔsecA2 mutant was also attenuated for growth in macrophages from phox$^{-/-}$ mice and from NOS2$^{-/-}$ mice. These mice are defective in the reactive oxygen intermediate (ROI)-generating phagocyte oxidase or the reactive nitrogen intermediate (RNI) generating inducible nitric oxide synthase, respectively. This indicated a role for SecA2 in the intracellular growth of *M. tuberculosis* that is independent of protecting against these ROI or RNI. Macrophages infected with the ΔsecA2 mutant produced higher levels of TNF-α, IL-6, RNI and IFN-γ induced MHC class II. This demonstrates a function for *M. tuberculosis* SecA2 in suppressing macrophage immune responses, which could explain the role of SecA2 in intracellular growth. Our results provide another example of a relationship between *M. tuberculosis* virulence and inhibition of the host immune response.

Introduction

*Mycobacterium tuberculosis*, the causative agent of tuberculosis, is one of the most successful bacterial pathogens of all time. The global burden of tuberculosis is at its highest level ever and includes an increasing number of multiple drug resistant *M. tuberculosis* infections (World Health Organization, 2005). Novel anti-tuberculosis prevention and treatment measures are needed to control this health crisis, and a complete understanding of *M. tuberculosis* pathogenesis will help achieve this goal.

*M. tuberculosis* is inhaled and taken up by unactivated host macrophages where it is able to replicate and survive. Much remains to be learned about how *M. tuberculosis* avoids host defenses in these macrophages. The processes involved are likely complex and multifactorial. Among the properties implicated in *M. tuberculosis* survival in macrophages is the ability of the bacillus to block acidification of the phagocytic vacuole, to block phagosome-lysosome fusion, and to resist reactive oxygen and nitrogen intermediates (ROI and RNI) (Koul et al., 2004; Smith, 2003).

The early innate immune response to *M. tuberculosis* includes Toll-like receptor (TLR) stimulation of macrophages (Krutzik and Modlin, 2004; Quesniaux et al., 2004). TLR signaling leads to the secretion of RNI and pro-inflammatory cytokines that include TNF-α and IL-6. Later in infection, activation of host macrophages by an adaptive TH1 immune response occurs leading to the inhibition of intracellular growth and control of *M. tuberculosis* infection. IFN-γ is an important mediator of this response; it upregulates antimycobacterial processes and antigen presentation by macrophages (Flynn and Chan, 2001). One of the antimycobacterial effectors induced by IFN-γ is RNI, which is produced by the inducible nitric oxide synthase (NOS2), although other IFN-γ-dependent effector mechanisms exist (Chan et al., 1992; MacMicking et al., 1997; MacMicking et al., 2003). TNF-α is another cytokine that plays an integral role in host control of *M. tuberculosis* infection (Bean et al., 1999; Botha and Ryffel, 2003; Flynn et al., 1995). Among the many properties reported for TNF-α is that it can synergize with IFN-γ to induce potent antimycobacterial activity of macrophages (Chan et al., 1992; Flesch and Kaufmann, 1990; Flynn and Chan, 2001).

It is increasingly apparent that *M. tuberculosis* can limit the host immune response and macrophage activation, and that this inhibition is likely to be important to survival in macrophages (Koul et al., 2004). Although dependent on experimental conditions, there are several reports of macrophages infected with more virulent *M. tuberculosis* producing lower levels or activities of TNF-α and/or RNI in comparison to macrophages infected with less virulent or attenuated mycobacteria (Balcewicz-Sablinska et al., 1998; Beltan et al., 2000; Falcone et al., 1994; Reed et al., 2004; Shimono et al., 2003). In a more direct fashion *M. tuberculosis* has been shown to suppress expression of *Escherichia coli*-induced pro-inflammatory IL-12 (Nau et al., 2002). *M. tuberculosis* is also known to inhibit IFN-γ upregulation of genes including the major histocompatibility complex (MHC) class II genes (Fortune et al., 2005; Nagabhushanam et al., 2003; Noss et al., 2000; Pai et al., 2004). Inhibition of MHC class II reduces antigen presentation which has implications for development of an effective TH1 response in vivo.

A common theme in bacterial pathogenesis is the importance of protein export and secretion pathways of the pathogen to virulence. These pathways export proteins beyond the cytoplasm to the cell surface or secrete proteins out of the bacterium. Both surface and secreted proteins are exposed to the external environment. As a result, these proteins are ideally positioned to protect the bacterium from macrophage attack or to modify the host immune response to the *bacillus* (Coombes et al., 2004; Kurtz and Braunstein, 2005). Like all bacteria, *M. tuberculosis* has the conventional Sec pathway and Sec proteins for exporting proteins beyond the cytoplasm (Kurtz and Braunstein, 2005). More unusual is the presence of two SecA proteins (SecA1 and SecA2) in *M. tuberculosis* (Braunstein et al., 2001). The SecA2 protein of *M. tubercilosis* is an accessory secretion factor that promotes secretion of a subset of proteins that include superoxide dismutase (SodA) and catalase-peroxidase (KatG) (Braunstein et al., 2003). Both of these enzymes detoxify oxygen radicals: SodA converts superoxide to hydrogen peroxide and oxygen and KatG converts hydrogen peroxide to water and oxygen. KatG is also able to break down peroxynitrite which is a dangerous reaction product of superoxide and nitric oxide (Wengenack et al., 1999). SecA2 contributes to the virulence of *M. tuberculosis* as shown previously using a ΔsecA2 mutant of *M. tuberculosis* in a high-dose murine model of tuberculosis (Braunstein et al., 2003).

Described here are studies of the ΔsecA2 mutant of *M. tuberculosis* in an aerosol model of murine infection and in murine bone marrow derived macrophages. The results with the two models were consistent and revealed a role for SecA2 in promoting *M. tuberculosis* growth early in murine infection and in unactivated macrophages. Using macrophages from phox$^{-/-}$ and NOS2$^{-/-}$ mice we further showed that the role of SecA2 is not simply explained by a failure to resist ROI produced by the phagocyte oxidase or RNI produced by the inducible nitric oxide synthase. In comparing macrophage responses to infection with the ΔsecA2 mutant or parental H37Rv *M. tuberculosis*, we discovered that macrophages infected with the ΔsecA2 mutant were more activated on the basis of several criteria: increased TNF-α, IL-6, RNI, and IFN-γ regulated MHC class II. This indicates a role for SecA2 in *M. tuberculosis* inhibition of the immune response which is likely important to survival in the host and pathogenesis.

Materials and Methods

Bacterial Strains and Growth Conditions. The *Mycobacterium tuberculosis* strains used in this study H37Rv, mc23112 (ΔsecA2 mutant, stock derived from a single colony) and mc23116 (ΔsecA2, attB::secA2) (Braunstein et al., 2003) were grown in Middlebrook 7H9 broth (Difco) with 0.2% glycerol, 1×ADS (albumin dextrose saline) and 0.050% Tween 80 (Tw). When appropriate, the media was supplemented with the antibiotic kanamycin (20 µg/ml).

Animals. Female C57BL/6 mice were purchased from Charles River Laboratories. p47$^{phox-/-}$ mice were generated and maintained as described previously (Barry-Lane et al., 2001). gp91$^{phox-/-}$ mice and NOS2$^{-/-}$ mice were purchased from Jackson Laboratories. All mice were housed in sterile microbarrier cages and were given autoclaved food and water ad libitum. Both strains of phox$^{-/-}$ mice were maintained on an antibiotic oral suspension of sulfamethoxazole (200 mg/5 ml) and trimethoprim (40 mg/5 ml) (Hi-Tech Pharmacal) in their water to prevent opportunistic infections.

Aerosol Infection. Female C57BL/6 mice ages 38-45 days were used for the aerosol studies. The *M. tuberculosis* strains were cultured to mid-log phase (OD600~0.5-1.0). The cultures were washed one time and resuspended in phosphate buffered saline (PBS) with 0.05% Tween 80 (PBS-Tw) to a concentration of 1×10$^7$ CFU (Colony Forming Units)/ml. The bacterial suspension was placed into the nebulizer jar of a whole body exposure aerosol chamber (Mechanical Engineering Workshop, Madison, Wis.). Mice were exposed for 15 minutes with a chamber purge time of 20 minutes. At specific timepoints, four mice were sacrificed from each group by CO$_2$ asphyxiation and the lungs, livers and spleens removed and homogenized in PBS-Tw with 100 ng/ml cycloheximide and 50 µg/ml carbenicillin. The homogenates were plated onto 7H10 ADS glycerol plates with 10 mg/ml cycloheximide for CFU enumeration.

Macrophage Infections. Bone marrow derived macrophages were prepared from C57BL/6, p47$^{phox-/-}$, gp91$^{phox-/-}$, and NOS2$^{-/-}$ mice as follows. Mice were sacrificed by CO$_2$ asphyxiation and the femurs were removed. The cells were flushed out of the femurs using supplemented DMEM (Sigma) containing 10% heat-inactivated fetal bovine serum (HI-FBS), 2 mM glutamine and 1× non-essential amino acids (NEAA). Cells were washed twice and cultured in supplemented DMEM for 6 days in the presence of 20% L929 conditioned medium (LCM). After 6 days, the cells were removed using 5 mM EDTA (in PBS), washed twice with supplemented DMEM, and resuspended in supplemented DMEM with 10% LCM. The cells were then seeded into the wells of either an 8-well chamber slide ($2\times10^5$ macrophages/well), or a 24-well plate ($8\times10^5$ macrophages/well) and were allowed to adhere overnight before infection. In some experiments, the macrophages were pretreated for 24 hours with 10 ng/ml recombinant murine IFN-γ (rmIFN-γ Chemicon) before infection, M. tuberculosis strains were taken from mid-log growth phase and washed one time in PBS-Tw. Cells were resuspended in PBS-Tw and further diluted to the appropriate CFU/ml in supplemented DMEM. The bacteria were added at the appropriate concentration to the cell monolayers to achieve a multiplicity of infection (MOI) of 1 or 10. Macrophages were infected for 4 hours, at which time the monolayers were washed three times with supplemented DMEM to remove any non-cell associated bacteria, and then fresh media with 10% LCM was added back. At various timepoints, the media was removed from the wells and the cells were lysed with 0.1% Tween 80 and vigorous pipetting. Lysates were diluted in PBS-Tw and plated onto 7H10 ADS glycerol 0.05% Tw plates for enumeration of CFU.

RNI measurements. To measure RNI we used the Griess Reagent (Molecular Probes) and followed the manufacturer's protocol. Briefly, supernatants from infected macrophage monolayers were filter-sterilized twice using a 0.2 μm low-protein binding filter, and mixed 1:1 with Griess reagent. Samples were measured at 548 nm, and the values converted to μM nitrite using a standard curve generated with sodium nitrite.

In Vitro Sensitivity Assays. Bacteria were grown to mid-log phase in 7H9 ADS glycerol Tw, washed, and diluted to a density of approximately $1\times10^6$ CFU/ml in PBS-Tw. Percent killing was determined for each strain by comparing the number of CFU from treated samples to untreated samples. The following treatments were employed: heat shock (53° C. for 45 minutes) and acid pH (pH4.0 for 24 hours). In vitro ROI killing assays were performed using various compounds. We tested sensitivity to hypoxanthine/xanthine oxidase (0 and 3 hours): (250 μM hypoxanthine) (Sigma)/xanthine oxidase (0.1 U/ml xanthine oxidase) (Roche) in the presence or absence of catalase (1 U/ml) (Sigma), added to detoxify hydrogen peroxide generated (De Groote et al., 1997; Piddington et al., 2001). Other ROI generating compounds tested include hydrogen peroxide (0, 5, 10 mM for 4 hours), plumbagin (0.2 mM for 3.5, 7.5, 10.5 hours), pyrogallol (2 mM for 0, 1, and 4 hours), and cumene hydroperoxide (0.5 mM for 0, 1 and 4 hours) (Sigma). In vitro sensitivity to RNI was tested using spermidine nonoate (SPER/NO) (200 μM for 0 and 4 hours)(Alexis Biochemicals). All in vitro ROI and RNI assays were performed at 37° C.

Cytometric Bead Array (CBA). Infection of bone marrow derived macrophages was performed as described above, infecting cells at MOI of 1. Supernatants were collected from the infected macrophages at 24 hours post infection and filtered twice through a 0.22 μm low-protein binding filter and supernatants were stored at −80° C. CBA was performed using the Mouse Inflammation CBA Kit (BD Biosciences) according to the manufacturer's protocol. Samples were analyzed on a BD Biosciences FACSCalibur flow cytometer. The triplicate samples for each strain were averaged and the data is shown as the mean±standard deviation.

Quantitative Real Time-PCR (qRT-PCR) to measure IFN-γ responses of infected macrophages. Murine bone marrow-derived macrophages were prepared and infected as described above at an MOI of 10 for 3 hours, at which time unincorporated bacteria were washed off and fresh media added back to the monolayers. After 21 hours post-infection, the media was removed from the monolayers and replaced with fresh medium containing 2 ng/ml rmIFN-γ. After 15 hours of rmIFN-γ treatment, the supernatants were removed, and the monolayers lysed with TRizol reagent (Invitrogen). The human monocytic cell line THP-1 (ATCC TIB-202) was maintained in supplemented RPMI with 10% HI-FBS. To prepare the THP-1 cells for infection, they were washed twice in fresh RPMI with FBS, resuspended in RPMI with FBS containing 50 ng/ml phorbol myristate acetate (PMA) (Sigma), and seeded into 6-well tissue culture plates at $2\times10^6$ cells/well. After 24 hours PMA treatment, the cells were infected at an MOI of 10 in the presence of 200 ng/ml recombinant human IFN-γ (rhIFN-γ Pierce) for 4 hours. After uptake, the cells were washed and fresh media with rhIFN-γ was added. At 24 hours post-infection, the supernatant was removed from the infected monolayers and the cells were lysed with TRIzol. TRIzol lysates were processed for RNA extraction. RNA samples were reverse transcribed and Real-time PCR was performed using the Taq-Man sequence detection system with Absolute QPCR Mix (Applied Biosystems). Values were calculated based on standard curves generated for each gene. Normalization of samples was determined by dividing copies of MHC class II mRNA by copies of 18S rRNA. 18S probe (5'-TAMRA-CAAATTACCCACTC-CCGACCG-3' [SEQ ID NO:2]) and primers F (5'-GCT-GCTGGCACCAGACTT-3' [SEQ ID NO:3]) and R (5'-CG-GCTACCACATCCAAGG-3' [SEQ ID NO:4]); murine MHC class II (I-Ab) probe (5'-FAM-CGCAGCGCATACGATAT-GTGACCA-TAMRA-3' [SEQ ID NO:5]) and primers Rev (5'-CTGTCGTAGCGCACGTACT-3' [SEQ ID NO:6]) and For (5'-GGCGAGTGCTACTTCACCA-3' [SEQ ID NO:7]); human MHC class II (HLA-DRA) probe (5'-FAM-CTG-GACCCTTTGCAAGAACCCTTCCC-TAMRA-3' [SEQ ID NO:8]) and primers F (5'-TCCAATGAACGGAGTATCT-TGTGT-3' [SEQ ID NO:9]) and R (5'-TGAGATGACG-CATCTGTTGCT-3' [SEQ ID NO:10]) (Gehring et al., 2003; Wengenack et al., 1999).

Results

Figure 14:
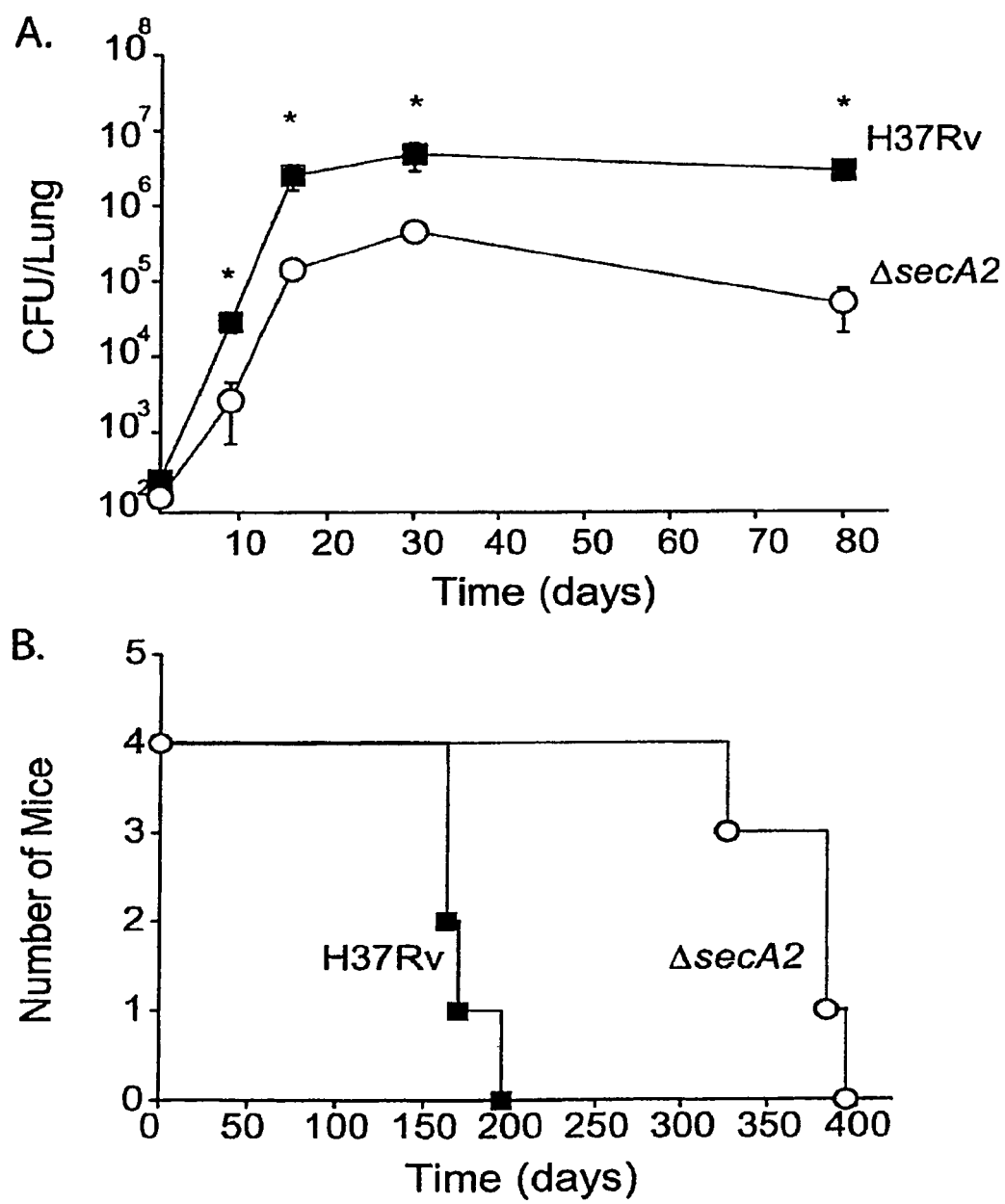
FIG. 14 is graphs of experimental results showing that the ΔsecA2 mutant of *M. tuberculosis* is attenuated in a low dose aerosol infection of C57BL/6 mice. Immunocompetent C57BL/6 mice were exposed in a whole body aerosol chamber to either *M. tuberculosis* H37Rv (■) or the ΔsecA2 mutant (○), each mouse receiving approximately 200 CFU (Colony Forming Units) per lung. Panel A: Mice were sacrificed at various timepoints post-infection and the growth of the strains assessed by plating for CFU from lung homogenates. The results are representative of two experiments. *p values compared to the ΔsecA2 mutant are p<0.005 by Student's t test. Panel B: Groups of 4 mice infected with either strain were monitored for survival.

The ΔsecA2 mutant is attenuated in the murine low-dose aerosol infection model. Previously, it was demonstrated that an in-frame and unmarked ΔsecA2 deletion mutant of M. tuberculosis is attenuated in mice following high-dose intravenous administration (Braunstein et al., 2001). To better characterize the phenotype of the ΔsecA2 mutant, we used a more natural low-dose aerosol exposure model infecting C57BL/6 mice with approximately 200 bacilli to the lungs, and included earlier time points than previously analyzed. Following infection with the ΔsecA2 mutant or the virulent M. tuberculosis parent H37Rv, groups of mice were sacrificed at times post-infection and the bacterial burden in the lungs, livers and spleens was enumerated by plating homogenates for colony forming units (CFU). We observed a typical growth pattern for H37Rv in the lungs of the mice: significant growth during the early phase of infection followed by a period of persistence in which the number of bacilli remained constant over time (Orme and Collins, 1994) (FIG. 14A). The transition between the growth and persistence phases correlates with the establishment of the TH1 response, a central feature of which is macrophage activation by IFN-γ (North and Jung, 2004; Orme and Collins, 1994). The ΔsecA2 mutant was defective in the early growth phase of the infection when compared to H37Rv. As early as nine days post-infection, the ΔsecA2 mutant had one log fewer bacilli in the lungs in comparison to H37Rv (FIG. 14A). This difference was maintained throughout the experiment, although both strains continued to grow to the day 16 time point. We also observed fewer CFU for the ΔsecA2 mutant in livers and spleens (0.5-1.0 log less) when compared to H37Rv (data not shown). During the latter phase of infection, the ΔsecA2 mutant resembled H37Rv in persisting although at the final 80 day time point the CFU burden in lungs of the secA2 mutant infected mice had dropped slightly. In addition to reduced bacillary load, mice infected with the ΔsecA2 mutant exhibited an increase in length of survival (mean survival of 372±29 days) in comparison to mice infected with H37Rv (mean survival of 173±16 days) (FIG. 14B).

Figure 15:
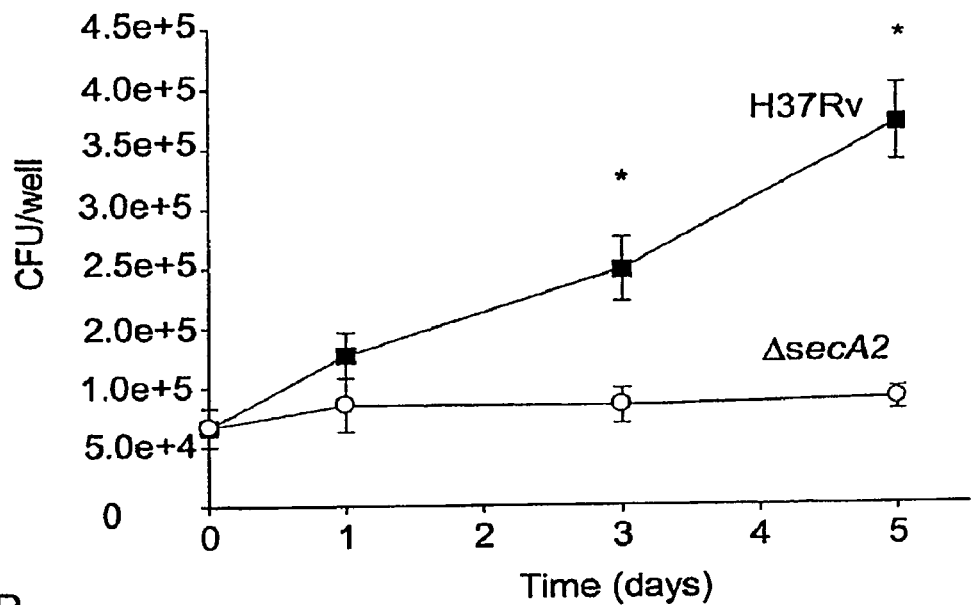
FIG. 15 is graphs of experimental results showing that the ΔsecA2 mutant of *M. tuberculosis* is attenuated in unactivated murine bone marrow derived macrophages. Unactivated murine bone marrow derived macrophages from C57BL/6 mice were infected at MOI=1 with (Panel A) *M. tuberculosis* H37Rv (■) or the ΔsecA2 mutant (○) and (Panel B) the ΔsecA2 mutant (○) or the ΔsecA2 complemented mutant (ΔsecA2, attB::secA2) (▲). CFU were determined by plating macrophage lysates at various timepoints post-infection. The infection was performed with triplicate wells for each strain per timepoint, and the error bars represent mean±standard deviation for the triplicate wells. Data shown are representative of more than 20 experiments for wild-type and the ΔsecA2 mutant, and five experiments for the complemented strain. *p values compared to ΔsecA2 are p<0.05 by Student's t test.
Figure 15:
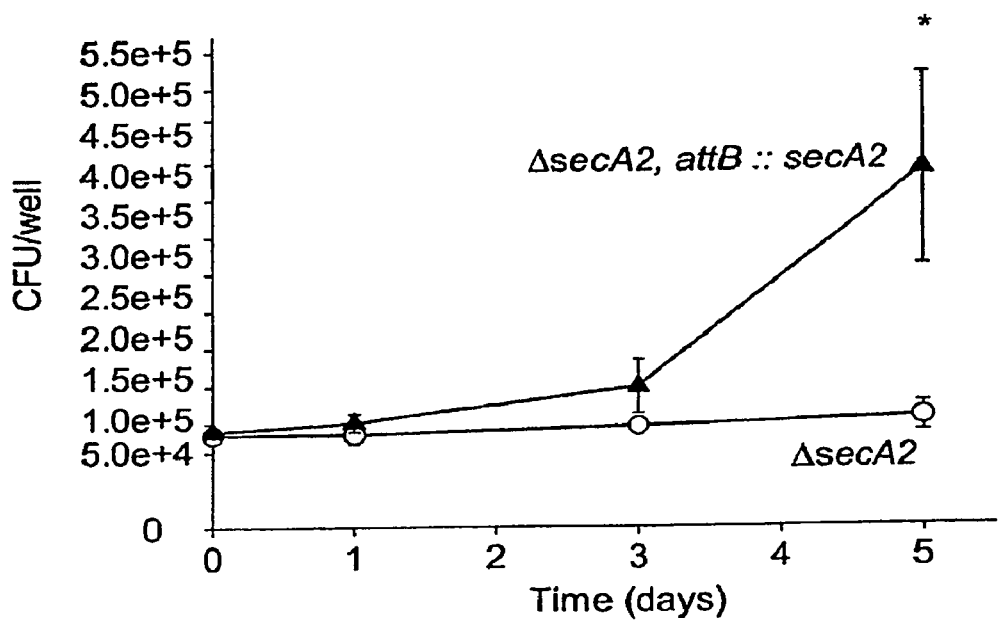

The ΔsecA2 mutant has an attenuated phenotype in unactivated macrophages but not in activated macrophages. The observed in vivo phenotype of the ΔsecA2 mutant indicated a role for SecA2 in the early phase of infection, during which *M. tuberculosis* is growing in macrophages. It was hypothesized that the ΔsecA2 mutant is defective for growth in unactivated macrophages. This hypothesis was tested by comparing the ability of the ΔsecA2 mutant and H37Rv to replicate within unactivated bone marrow derived macrophages from C57BL/6 mice. The macrophages were infected ex vivo, and after four hours uptake the monolayers were washed and fresh media added back. The growth of each strain was evaluated over a five day period by plating macrophage lysates for viable CFU. The ΔsecA2 mutant showed diminished growth in the macrophages and displayed up to one log less CFU by Day 5 (FIG. 15A). The intracellular growth defect of the ΔsecA2 mutant was complemented by introduction of a wild-type copy of secA2 on an integrating plasmid, which indicated that the mutant phenotype was due to the absence of secA2 (FIG. 15B).

Figure 16:
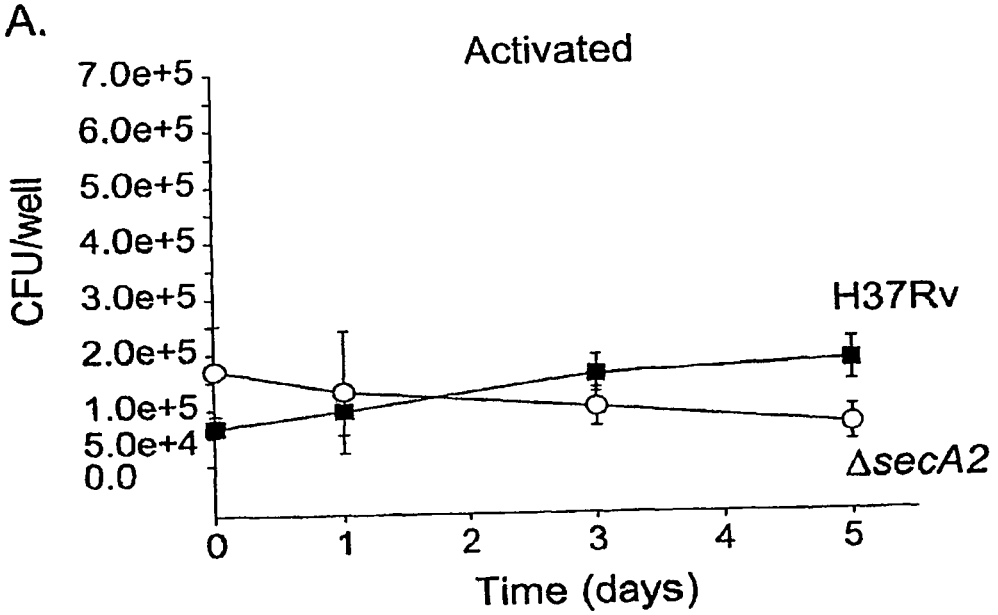
FIG. 16 is graphs of experimental results showing survival of the ΔsecA2 mutant in IFN-γ-treated murine bone marrow derived macrophages. In parallel experiments survival and growth of the ΔsecA2 mutant and H37Rv were examined in (Panel A) activated and (Panel B) unactivated murine bone marrow derived macrophages from C57BL/6 mice. Macrophages were activated by 24 hour pretreatment with 10 ng/ml rmINF-γ. The macrophages were infected at MOI=1 with H37Rv (■) or the ΔsecA2 mutant (○) as described. Graphs are shown as the average of 5 experiments ±SEM. *p values compared to ΔsecA2 mutant are p<0.05 by Student's t test.
Figure 16:
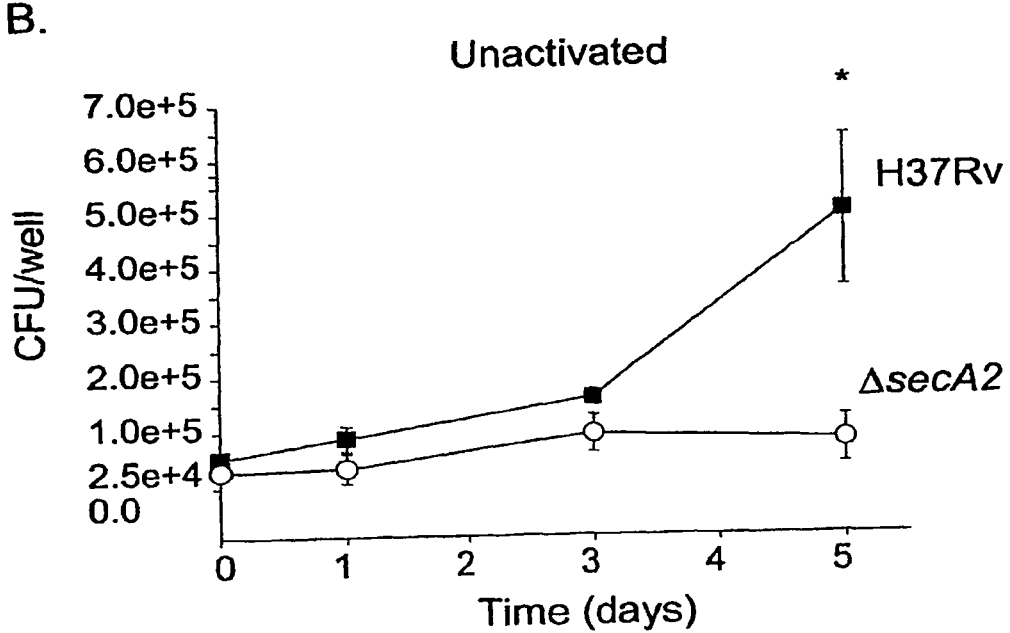

In contrast to unactivated macrophages which are permissive for *M. tuberculosis* growth, activated macrophages inhibit *M. tuberculosis* growth due to enhanced antimycobacterial activities (Chan et al., 1992; Flesch and Kaufmann, 1990; Flynn and Chan, 2001). We compared the ΔsecA2 mutant and 1H37Rv in murine bone marrow derived macrophages activated by 24 hours pretreatment with recombinant murine IFN-γ (rmIFN-γ). In the IFN-γ treated macrophages, H37Rv failed to grow but survived over time, and the ΔsecA2 mutant behaved similarly (FIG. 16A). Infection of unactivated macrophages was performed in parallel and again revealed an intracellular growth defect of the ΔsecA2 mutant (FIG. 16B).

These results reveal a role for SecA2 in promoting *M. tuberculosis* growth in unactivated macrophages but no apparent role for SecA2 in *M. tuberculosis* survival in activated macrophages. They are consistent with the pattern of growth in vivo, where the ΔsecA2 mutant exhibited reduced growth in the lungs of infected mice in the early growth phase of infection and then behaved similarly to H37Rv after the onset of the TH1 immune response and concomitant macrophage activation.

Figure 17:
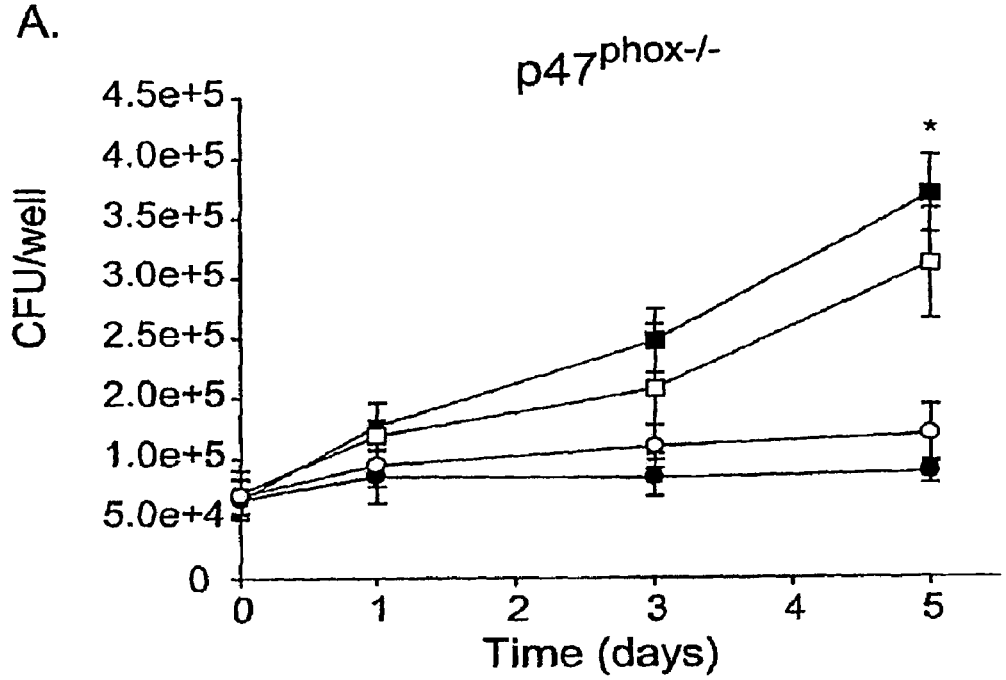
FIG. 17 is graphs of experimental results showing the ΔsecA2 mutant is attenuated in bone marrow derived macrophages from mice defective in components of the phagocyte oxidase (phox$^{-/-}$). Unactivated bone marrow derived macrophages from C57BL/6 mice and from either (A) p47$^{phox-/-}$ (B) gp91$^{phox-/-}$ were infected in parallel at MOI=1 with *M. tuberculosis* H37Rv (in C57BL/6 macrophages=■; in phox$^{-/-}$ macrophages ○) and the ΔsecA2 mutant (in C57BL/6 macrophages=●; in phox$^{-/-}$ macrophages ○). Graphs are shown as the average of multiple experiments (six for p47$^{phox-/-}$, three for gp91$^{phox-/-}$)±standard error of the means (SEM). *p values compared to ΔsecA2 are p<0.05 by Student's t test.
Figure 17:
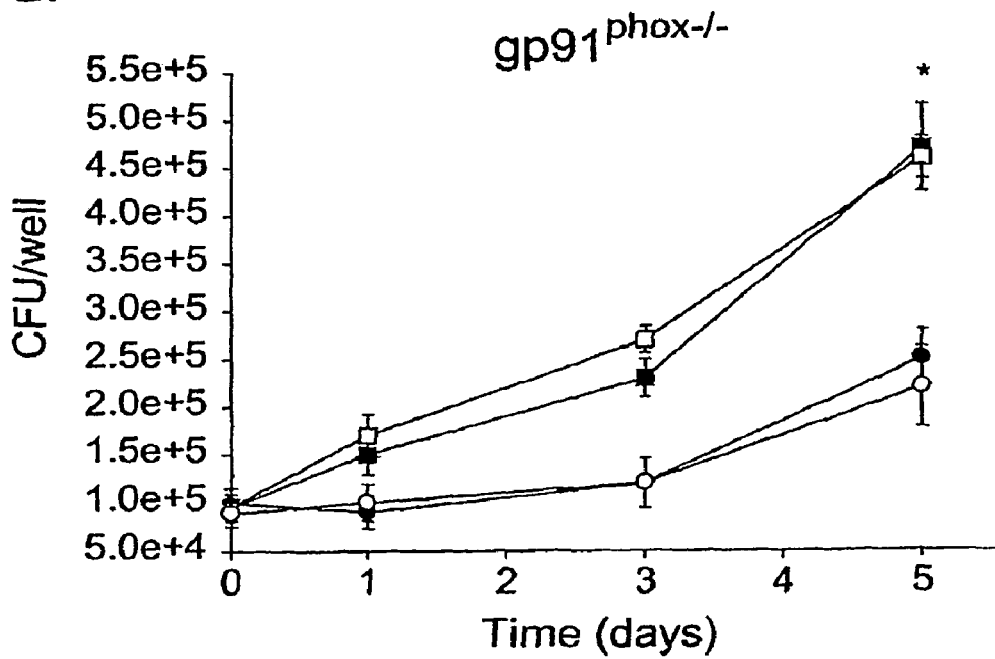

The ΔsecA2 mutant has an attenuated phenotype in oxidative burst deficient macrophages. It was previously reported that the ΔsecA2 mutant of *M. tuberculosis* is defective in secreting the antioxidant enzymes SodA and KatG (Braunstein et al., 2003). *M. tuberculosis* is relatively resistant to ROI (Chan et al., 1992) which could be an important property for intracellular survival in the face of the macrophage oxidative burst, and the SecA2-dependent secreted SodA and KatG are among the *M. tuberculosis* molecules implicated in this resistance (Smith, 2003). Whether the sole role of SecA2 in macrophage growth is to protect the bacillus from the oxidative burst during intracellular infection was tested. Bone marrow derived macrophages from p47$^{phox-/-}$, gp91$^{phox-/-}$, and C57BL/6 mice were prepared and infected in parallel with the ΔsecA2 mutant or H37Rv. These phox$^{-/-}$ mice lack different components of the phagocyte oxidase complex, which is responsible for the oxidative burst of macrophages (Nauseef, 2004). In these oxidative burst deficient macrophages, the ΔsecA2 mutant showed the same growth defect as observed in wild-type C57BL/6 macrophages (FIG. 17). This indicates that SecA2 contributes to intracellular growth even in the absence of an oxidative burst. Consequently, SecA2 must have a function in intracellular growth other than just protecting the bacillus from ROI generated during the oxidative burst.

As an independent assessment of the role of SecA2 in protecting against oxygen radicals, in vitro sensitivity to a variety of ROI species was compared between the ΔsecA2 mutant and H37Rv. Among the compounds tested were pyrogallol and hypoxanthine/xanthine oxidase; both of these treatments generate extracellular superoxide. Plumbagin (cytoplasmic superoxide generator), hydrogen peroxide, and cumene hydroperoxide were also tested. In all cases, the ROI treatments showed an equivalent degree of killing for the ΔsecA2 mutant and H37Rv (data not shown). The strains were also tested for their sensitivity to other stresses including acid pH and heat shock. Again, no differences in killing were apparent. The unaltered in vitro sensitivities of the ΔsecA2 mutant in combination with the data from phox$^{-/-}$ macrophages suggested that the role of SecA2 in promoting growth in macrophages is not solely to protect the bacteria from damaging ROI and involves other mechanisms.

Figure 18:
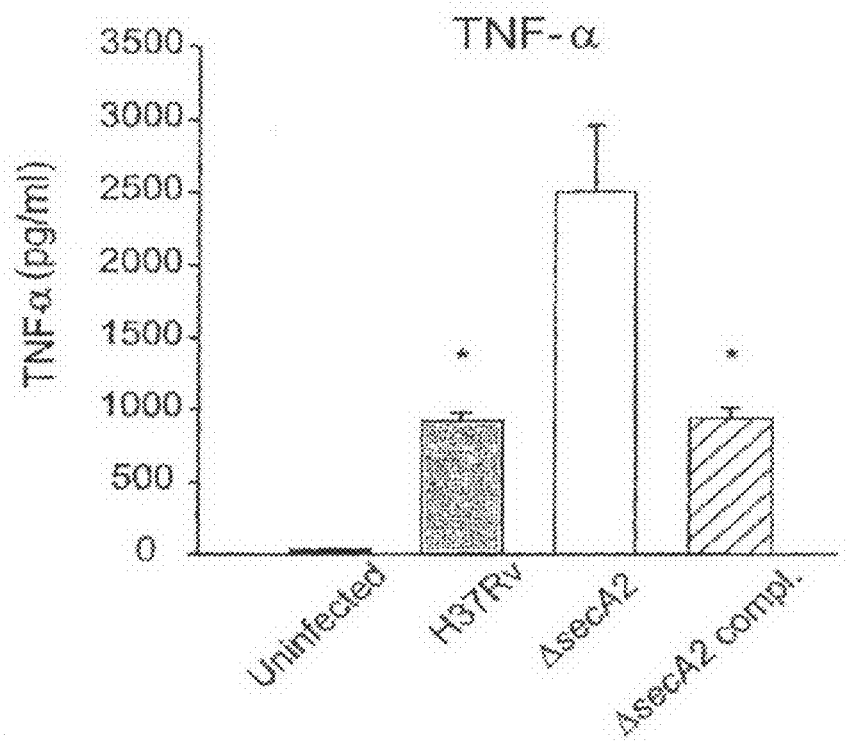
FIG. 18 is graphs of experimental results showing cytokine release from infected bone marrow derived macrophages. Cytokines were measured using the Cytometric Bead Array kit (BD Biosciences). Bone marrow derived macrophages from C57BL/6 mice were infected at MOI=1 in triplicate. Supernatants were collected at 24 hours post-infection and assayed for cytokines. Graphs present levels of cytokine for (Panel A) TNF-α or (Panel B) IL-6 uninfected macrophages (black bar), or those infected with H37Rv (grey bar), the ΔsecA2 mutant (white bar), or the ΔsecA2 complemented strain (hatched bar), with error bars depicting standard deviation (SD) of triplicate samples. Data shown are representative of eight experiments. *p values compared to ΔsecA2 mutant are p<0.05 by Student's t test.
Figure 18:
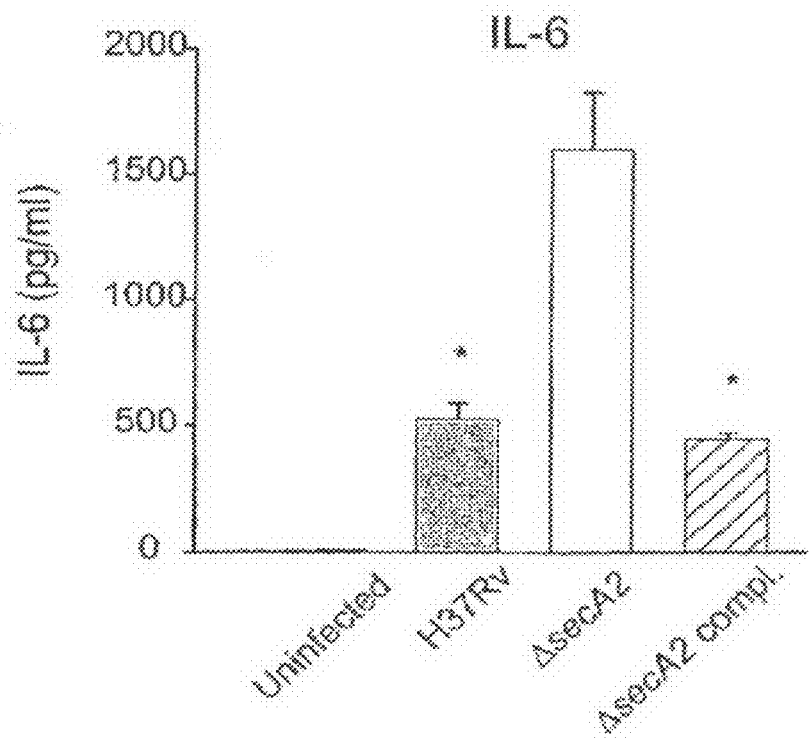

Macrophages infected with the ΔsecA2 mutant release higher levels of pro-inflammatory cytokines and RNI. To determine if the SecA2-dependent secretion pathway contributes to *M. tuberculosis* inhibition of host immune responses, cytokine production was compared in macrophages infected with the ΔsecA2 mutant or H37Rv. Bone marrow derived macrophages from C57BL6 mice were infected as before and 24 hours post-infection supernatants were assayed for cytokine production using the Cytometric Bead Assay (BD Biosciences). Macrophages infected with the ΔsecA2 mutant produced more TNF-α and IL-6 than those infected with H37Rv (FIG. 18), with an average difference of 2.5 fold for TNF-α and 3.5 fold for IL-6. Introduction of an integrated plasmid expressing wild-type secA2 complemented the increased cytokine production phenotype of the ΔsecA2 mutant.

Figure 19:
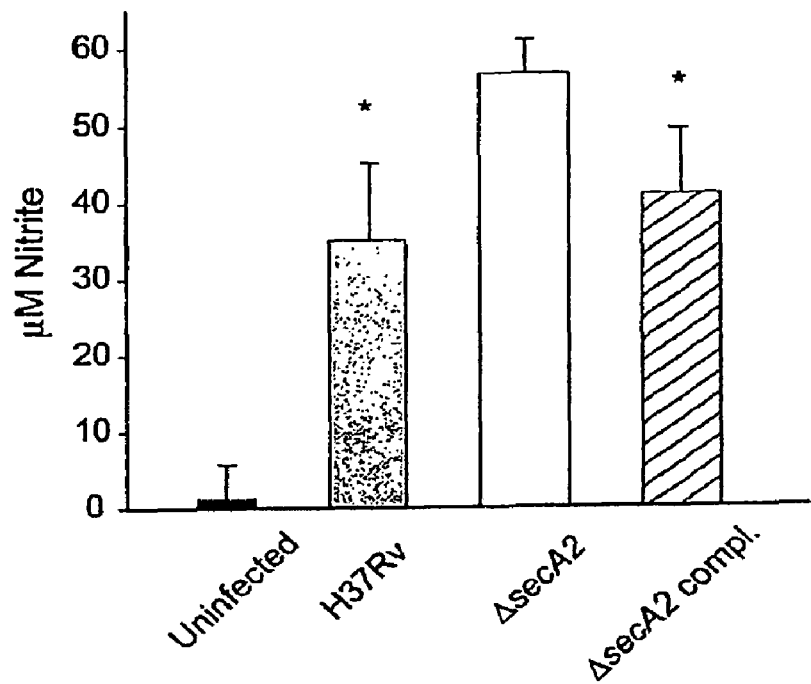
FIG. 19 is graphs of experimental results showing reactive Nitrogen Intermediates (RNI) produced by infected bone marrow derived macrophages. RNI was measured using the Griess reagent. Infections were performed at MOI=10 and samples were collected at 72 hours post-infection for unactivated macrophages (Panel A) and 24 hours post-infection for IFN-γ-activated macrophages (Panel B). Bars show the average of triplicate samples for uninfected cells (black bars), or those infected with H37Rv (grey bars), the ΔsecA2 mutant (white bars), or the ΔsecA2 complemented strain (hatched bars), with error bars depicting standard deviation (SD) of triplicate samples. Data shown are representative of three experiments. *p values compared to ΔsecA2 mutant are p<0.05 by Student's t test.
Figure 19:
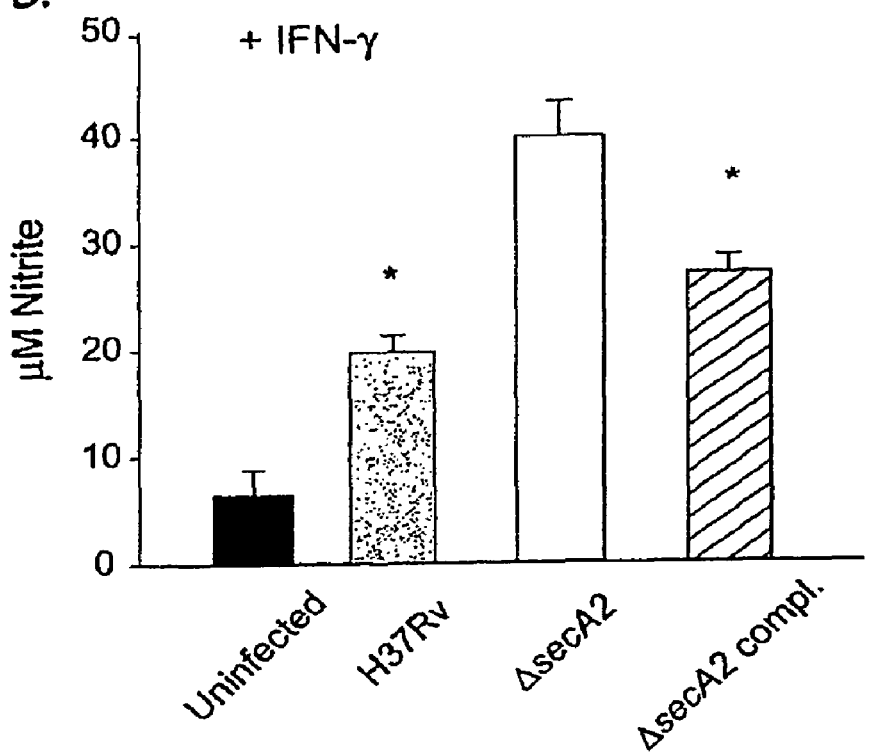

Production of RNI was also assayed in the supernatants of infected macrophages using the Griess Reagent which measures nitrite, the oxidation product of nitric oxide. Measurements were taken at 48, 72 and 96 hours post-infection. The macrophages infected with the ΔsecA2 mutant produced more RNI at all time points compared to macrophages infected with H37Rv (FIG. 19A, data shown for 72 hours), with an average difference of 1.5 fold. In the same experiments at 0, 4 and 24 hours post-infection, the levels of ROI in the cells was also measured. There were no apparent differences in level of ROI between cells infected with the ΔsecA2 mutant or H37Rv (data not shown). Also tested was the level of RNI production by infected cells pretreated with IFN-γ 24 hours prior to infection, which upregulates RNI production. As expected, there was an overall increase in RNI production in cells pretreated with IFN-γ compared to untreated cells. At 24 hours post-infection macrophages infected with the ΔsecA2 mutant again exhibited higher levels of RNI in the supernatant (FIG. 19B). The increased RNI production observed following infection with the ΔsecA2 mutant in the absence and presence of IFN-γ was complemented by introduction of a wild-type copy of secA2.

It is important to note that in these experiments the number of CFU in macrophage lysates following the 4 hour infection period was equivalent for both strains. The above results suggest that, in comparison to H37Rv, the ΔsecA2 mutant is defective in the ability to inhibit macrophage production of immunostimulatory molecules. The end result being more highly activated macrophages upon infection with the ΔsecA2 mutant.

Figure 20:
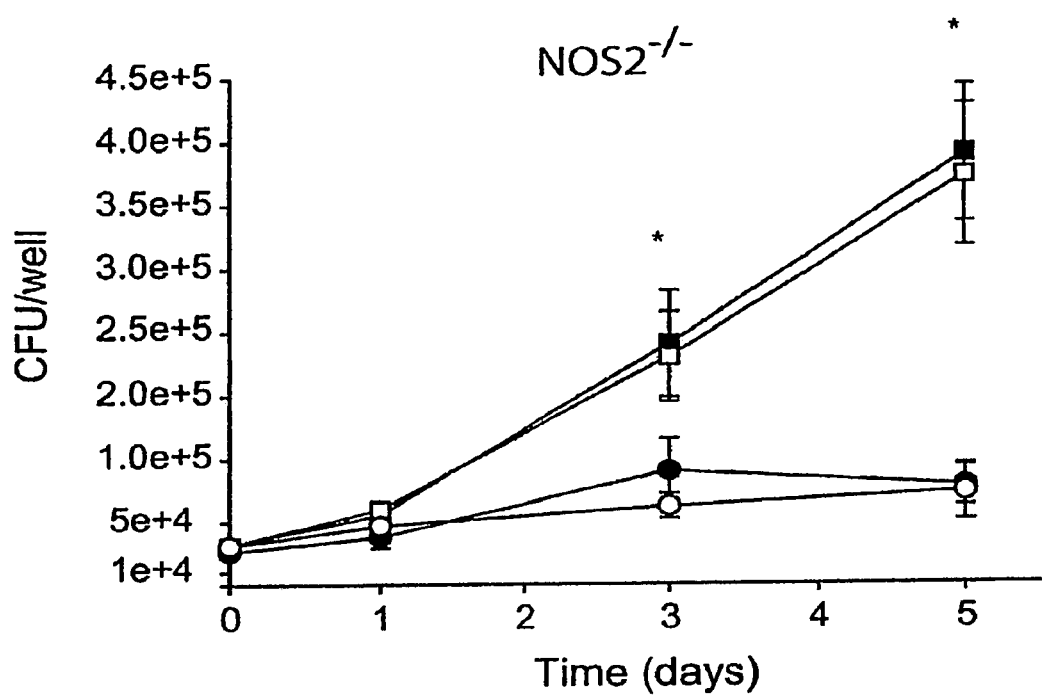
FIG. 20 is a graph of experimental results showing the ΔsecA2 mutant is attenuated in bone marrow derived macrophages from mice defective in inducible nitric oxide synthase (NOS2). Unactivated bone marrow derived macrophages from C57BL/6 mice and from NOS2$^{-/-}$ mice were infected in parallel at MOI=1 with $M.$ $tuberculosis$ H37Rv (in C57BL/6 macrophages ■; in NOS2$^{-/-}$□) and the ΔsecA2 mutant (in C57BL/6 macrophages ●; in NOS2$^{-/-}$ macrophages ○) as described above. Graphs are shown as the average of four experiments±standard error of the means (SEM). *p values compared to ΔsecA2 are p<0.05 by Student's t test.

The ΔsecA2 mutant has an attenuated phenotype in NOS2$^{-/-}$ macrophages. Given the antimycobacterial activity of RNI, it was possible that the increased levels of RNI observed were alone responsible for the growth defect of the ΔsecA2 mutant in macrophages. To test this idea, the growth of the ΔsecA2 mutant and H37Rv was examined in unactivated macrophages from NOS2$^{-/-}$ mice, which lack the inducible nitric oxide synthase and are defective for the nitrosative burst (MacMicking et al., 1997a). The ΔseqA2 mutant still exhibited a growth defect in NOS2−/− macrophages that was equivalent to the defect observed in macrophages from C57BL/6 mice (FIG. 20). This data indicated that the role of SecA2 in intracellular growth involves functions other than protecting against reactive nitrogen intermediates.

As was done for ROI, in vitro sensitivity of the ΔsecA2 mutant and H37Rv to NO generated by spermadine nonoate (SPER/NO) was also examined. Treatment with SPER/NO led to an equivalent degree of killing of the ΔsecA2 mutant and H37Rv (data not shown). The in vitro sensitivity result taken together with the observed growth defect of the ΔsecA2 mutant in NOS2$^{-/-}$ macrophages suggests that the role of SecA2 in intracellular growth is not solely to protect against RNI.

Figure 21:
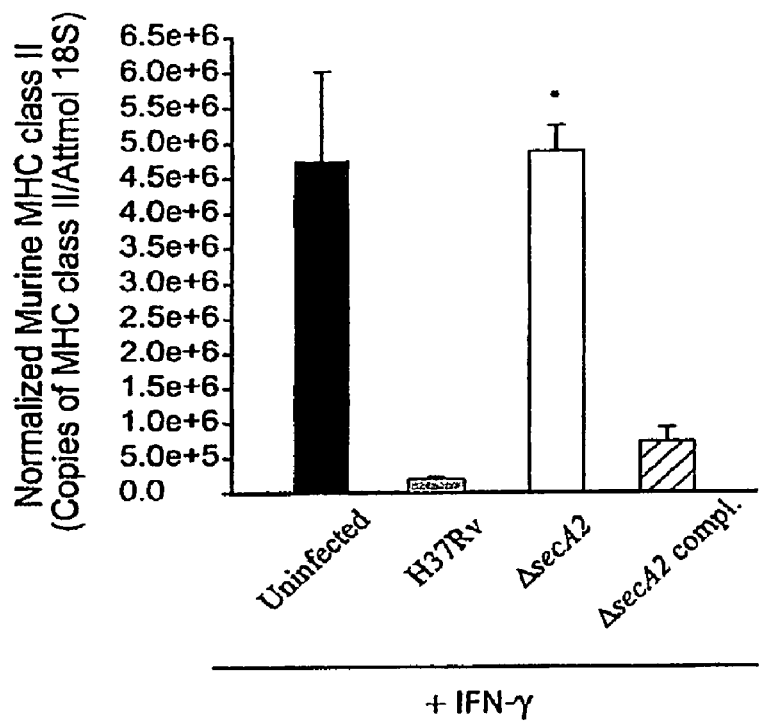
FIG. 21 is graphs of experimental results showing the inhibition of MHC class II expression measured by quantitative Real-Time PCR. Host mRNA expression was determined by qRT-PCR of RNA made from murine bone marrow derived macrophages or THP-1 cells. Cells were infected with $M.$ $tuberculosis$ strains at MOI-10 and stimulated with rIFN-γ, and uninfected cells were similarly treated with rIFN-γ. For murine macrophages the cells were infected with $M.$ $tuberculosis$ strains and let sit for 21 hours prior to addition of 2 ng/ml rmIFN-γ. RNA was sampled at 15 hours post rIFN-γ addition. For THP-1 cells, the cells were simultaneously infected with $M.$ $tuberculosis$ and treated with 200 ng/ml rhIFN-γ RNA was sampled at 24 hours post-infection. The qRT-PCR samples were normalized to an internal 18S control. Bars represent the normalized MHC class II levels of triplicate infections performed on a single day with error bars showing standard deviation. Data is shown as a representative of five experiments for each (A) murine bone marrow derived macrophages and (B) THP-1 cells. Samples are shown as uninfected (black bars), or cells infected with H37Rv (grey bars), the ΔsecA2 mutant (white bars), or the complemented strain (hatched bars). *p values compared to wild type and complemented are p<0.003 by Student's t test.
Figure 21:
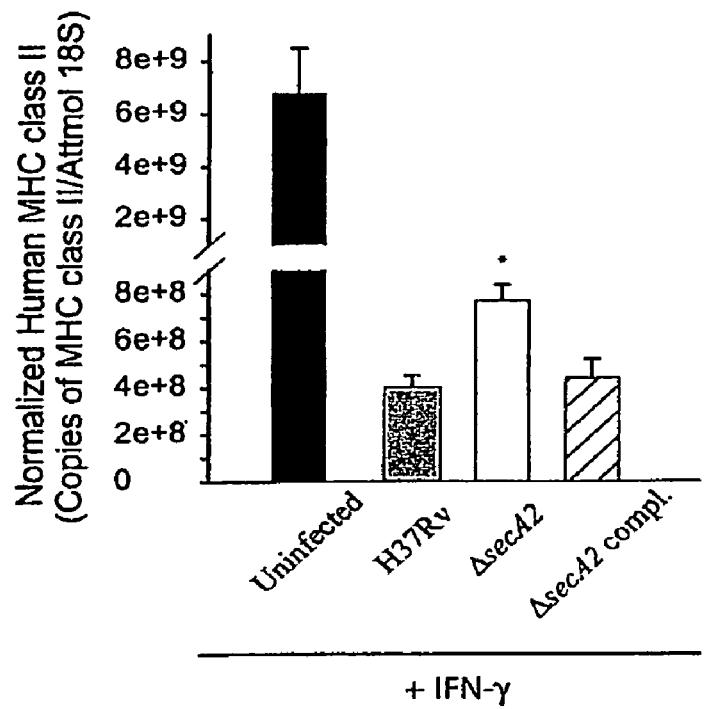

The ΔsecA2 mutant is associated with higher IFNγ induced MHC class II expression. Having demonstrated that macrophages infected with the ΔsecA2 mutant produced higher levels of cytokine and RNI in comparison to H37Rv infected macrophages, the inhibition of other macrophage responses was altered by the ΔsecA2 mutation was then evaluated. Multiple laboratories have demonstrated that *M. tuberculosis* inhibits the expression of several IFN-γ regulated genes of the host. Among these genes are the IFN-γ induced MHC class II genes required for antigen presentation (Nagabhushanam et al., 2003; Noss et al., 2000; Pai et al., 2004). To test for a role of SecA2 in *M. tuberculosis* inhibition of IFN-γ responses, employed were two different systems previously used to study this IFN-γ inhibition: primary murine macrophages and the human monocytic cell line THP-1. Murine bone marrow derived macrophages were pre-infected with the ΔsecA2 mutant, H37Rv, or the complemented strain at MOI 10 for 24 hours followed by stimulation with rmIFN-γ. After 15 hours of IFN-γ treatment, expression of MHC class II (IA-b) transcript was measured by quantitative Real Time PCR (qRT-PCR). As expected, IFN-γ treatment of uninfected cells increased MHC class II transcript and H37Rv inhibited the IFN-γ induction of MHC class II. In contrast, infection with the ΔsecA2 mutant did not reduce the level of MHC class II to the same degree as H37Rv (FIG. 21A). This difference between the ΔsecA2 mutant and H37Rv in the level of IFN-γ induced MHC class II was at least 2.0 fold greater with the ΔsecA2 mutant in five separate experiments (p=0.008 by Mann-Whitney test). Similar experiments were performed with human THP-1 cells. In these experiments rhIFN-γ was added to the cells at the time of infection with either the ΔsecA2 mutant, H37Rv, or complemented strain. Expression of MHC class II (HLA-DR) transcript was measured by qRT-PCR on samples collected at 24 hours post-infection. Again, infection with the ΔsecA2 mutant did not reduce the level of MHC class II to the same degree as H37Rv. This difference between the ΔsecA2 mutant and H37Rv in the level of IFN-γ induced MHC class II was reproducible with the ΔsecA2 mutant exhibiting an average 1.5 fold difference in HLA-DR transcript level over five independent experiments (p=0.00003 by Student's t test). The phenotypes of the ΔsecA2 mutant in both murine macrophages and THP-1 cells were complemented by the introduction of a wild-type copy of secA2. This data provided another example of SecA2 functioning in the process(es) of *M. tuberculosis* inhibition of host immune responses.

Discussion

The accessory secretion factor SecA2 contributes to *M. tuberculosis* virulence. As shown here with a natural low-dose aerosol model of infection, as early as nine days post-infection the ΔsecA2 mutant had a lower bacterial burden in the lungs of mice in comparison to the parental *M. tuberculosis* H37Rv. The attenuated phenotype of the mutant occurred during the early growth phase of infection, when *M. tuberculosis* is primarily growing in unactivated macrophages. Consistent with this result, the ΔsecA2 mutant had a growth defect in unactivated murine bone marrow macrophages when compared to H37Rv. It should be noted that the ΔsecA2 mutant does not display any significant growth defect when grown in broth media (Braunstein et al., 2001). In contrast to the phenotype in unactivated murine macrophages, the ΔsecA2 mutant did not exhibit a phenotype in IFN-γ activated macrophages. The experiments in vitro with primary murine macrophages appear to reflect the phenotypes observed in vivo in the murine model of infection. Since SecA2 is an accessory secretion factor, the role of SecA2 could be the proper secretion or surface localization of *M. tuberculosis* proteins required for intracellular growth. Previously, SodA and KatG were identified as proteins whose secretion into culture media depends on SecA2 (Braunstein et al., 2003). Since both of these proteins are antioxidants, the simple hypothesis was considered that SecA2 promotes detoxification of ROI and thereby protects the *bacillus* from the oxidative burst of macrophages to promote intracellular growth. Macrophage generated ROI could have direct antimicrobial effects or indirect effects involving alterations in host cell signaling pathways (Nathan, 2003; Thannickal and Fanburg, 2000). There is a precedent for exported superoxide dismutases contributing to virulence in bacterial pathogens (Battistoni, 2003), and various experiments suggest roles for *M. tuberculosis* SodA, KatG, and a surface localized superoxide dismutase, SodC, in pathogenesis and protection against the oxidative burst of macrophages (Dussurget et al., 2001; Edwards et al., 2001; Manca et al., 1999; Ng et al., 2004; Piddington et al., 2001). However, when the ΔsecA2 mutant was tested in phox$^{-/-}$ macrophages, it exhibited a growth defect equivalent to that observed in wild-type C57BL/6 macrophages. In addition, efforts to detect altered in vitro sensitivity of the ΔsecA2 mutant to ROI species, including extracellularly generated superoxide, were unsuccessful. Taken together, these experiments do not reveal a role for SecA2 in protecting against the oxidative burst and they indicate an alternate function of SecA2 in intracellular growth.

Yet, the possibility that SecA2 contributes to ROI resistance cannot be entirely ruled out. A role in protecting against ROI in macrophages and in vitro could have been masked by the other function(s) of SecA2 in intracellular growth and/or redundant ROI resistance mechanisms of *M. tuberculosis*. Furthermore, even in the absence of phagocyte oxidase there are still reactive oxygen species generated in the cell through mitochondrial electron transport. The possibility that mitochondrial generated ROI contribute to the phenotypes of the ΔsecA2 mutant cannot be ruled out.

The role that SecA2 plays in modulating the immune response was also assessed. It is becoming evident that virulent *M. tuberculosis* inhibits innate and adaptive immune responses. In regard to innate immune responses, *M. tuberculosis* has been shown to inhibit macrophage production of IL-12 in a co-infection assay (Nau et al., 2002). In addition, there is an emerging trend that virulent *M. tuberculosis* strains elicit reduced levels of pro-inflammatory cytokines (including TNF-α and IL-6) and RNI from macrophages than less virulent *M. tuberculosis* strains. This phenomenon has been described for the hypervirulent HN878 strain of *M. tuberculosis* and the hypervirulent mcel mutant of *M. tuberculosis* (Manca et al., 2004; Reed et al., 2004; Shimono et al., 2003). There are also reports of virulent *M. tuberculosis* eliciting lower levels or activities of cytokine and RNI from macrophages than attenuated and avirulent mycobacteria (Balcewicz-Sablinska et al., 1998; Beltan et al., 2000; Falcone et al., 1994; Freeman et al., 2006). However, it must be noted that for TNF-α a correlation between increased mycobacterial virulence and reduced cytokine production has not been a universal finding (Byrd, 1997; Engele et al., 2002; Rao et al., 2005; Silver et al., 1998). In regard to adaptive responses, *M. tuberculosis* inhibits macrophage responses to IFN-γ stimulation, such as the upregulation of MHC class II (Fortune et al., 2004; Nagabhushanam et al., 2003; Noss et al., 2000; Pai et al., 2004). MHC class II and presentation of mycobacterial antigens to CD4+ T cells is an essential component of the adaptive immune response to *M. tuberculosis* (Flynn and Chan, 2001).

In this study, macrophages infected with the ΔsecA2 mutant produced significantly greater levels of TNF-α, IL-6 and RNI than macrophages infected with H37Rv. This suggested a function for SecA2 in inhibiting the innate immune response. IL-12 production by infected macrophages could not be detected. The increased level of IFN-γ induced MHC class II message observed with the ΔsecA2 mutant versus H37Rv suggested an additional role for SecA2 in suppressing the adaptive immune response. This is the first report of a *M. tuberculosis* mutant with a defect in the inhibition of IFN-γ responses.

These immunomodulatory activities of SecA2 are likely important to *M. tuberculosis* virulence. All of the host molecules identified as being regulated by SecA2 are demonstrated to contribute to the control of tuberculosis in the mouse model. Mice deficient in TNF-α, IL-6, NOS2, or CIITA (MHC class II transcriptional regulator) are all more permissive for *M. tuberculosis* infection as shown by increased bacterial burden in organs and decreased length of survival in comparison to infection of wild-type mice (Bean et al., 1999; Flynn et al., 1995; MacMinking et al., 1997b; Repique et al., 2002; Saunders et al., 2000). Immunosuppression by SecA2 may influence the course of *M. tuberculosis* infection in many ways including the establishment of a permissive environment for intracellular growth in macrophages and limiting antigen presentation in the host. By infecting NOS2$^{-/-}$ macrophages with the ΔsecA2 mutant, it was demonstrated that suppression of RNI was not the only important factor regulated by SecA2 for promoting intracellular growth. The attenuated phenotype of the ΔsecA2 mutant in macrophages and mice appears to be a reflection of an imbalance in multiple cytokines and effector mechanisms, possibly including molecules we have yet to identify. Interestingly, all four of the molecules upregulated by macrophages infected with the ΔsecA2 mutant are associated with Toll like receptor 2 (TLR2) and Myeloid differentiation factor 88 (MyD88) signaling pathways in host cells. To varying degrees TNF-α, IL-6 and RNI are induced by mycobacterial stimulation of TLR2-dependent MyD88-dependent pathways (Brightbill et al., 1999; Heldwein et al., 2003; Jang et al., 2004; Nicolle et al., 2004; Reiling et al., 2002; Shi et al., 2005; Shi et al., 2003; Underhill et al., 1999). Thus, an increased ability of the ΔsecA2 mutant to signal through TLR2-MyD88-dependent pathways could account for the increased macrophage responses. However, there are alternate explanations given the complexities of cell signaling. Interestingly, there is also a role for TLR2 in the process of *M. tuberculosis* inhibition of IFN-γ induced MHC class II (Fortune et al., 2004; Gehring et al., 2003; Noss et al., 2001). However, our observation that infection with the ΔsecA2 mutant led to higher IFN-γ induced MHC class II message than infection with H37Rv is opposite to what would be predicted by increased TLR2 signaling. TLR2-independent pathways of *M. tuberculosis* inhibition of IFN-γ responses have also been identified in which SecA2 could be involved (Fortune et al., 2004; Quesniaux et al., 2004). Alternatively, increased TNF-α levels generated by the ΔsecA2 mutant could synergize with IFN-γ to promote the observed increase in MHC class II (Watanabe and Jacob, 1991).

Modification of the immune response is a strategy used by other bacterial pathogens to survive in the host, and the bacterial factors involved are often secreted and surface proteins localized by specialized secretion systems (Coombes et al., 2004). Currently, there are two known specialized secretion systems in *M. tuberculosis*: the SecA2-dependent system and the ESAT-6/Snm system (Kurtz and Braunstein, 2005). Interestingly, the ESAT-6/Snm system which localizes the small ESAT6 and CFP-10 proteins has also been reported to contribute to immunosuppression (MacGurn et al., 2005; Stanley et al., 2003). *M. tuberculosis* mutants lacking the snm4 (Rv3877) and snm9 (Rv3615c) components of the ESAT-6 system elicit increased levels of TNF-α, RNI and IL-12 by macrophages. Further, *M. tuberculosis* snm mutants exhibit a growth defect in unactivated macrophages and an early growth phenotype in mice (Fortune et al., 2005; Guinn et al., 2004; Hsu et al., 2003; MacGurn et al., 2005; Stanley et al., 2003). There is no immediate explanation for the similarity in snm and ΔsecA2 mutant phenotypes, since the ΔsecA2 mutant secretes ESAT-6 (data not shown).

Because SecA2 is a secretion factor, its role in immunomodulation is most likely related to proper secretion or cell wall localization of an immunosuppressive factor. However, all of the proteins localized by SecA2, particularly cell wall proteins, are not yet known. The mycobacterial cell wall is a complex structure that contains many diverse molecules with reported immunomodulatory properties (Karakousis et al., 2004). These include several surface molecules reported to influence the production of inflammatory TNF-α, IL-6 and/or RNI such as surface lipoproteins, lipoarabinomannan (LAM) and its precursor lipomannan (LM), phthiocerol dimycocerosates (PDIMs or DIMs), and modified trehalose dimycolate (Adams et al., 1993; Barnes et al., 1992; Brightbill et al., 1999; Dao et al., 2004; Krutzik and Modlin, 2004; Quisniaux et al., 2004a, b; Rao et al., 2005; Rousseau et al., 2004). The increased immune response elicited by the ΔsecA2 mutant could be explained by different amounts of immunoregulatory molecules in the cell wall or an altered cell wall structure with greater exposure of stimulatory molecules that interact with host receptors, such as TLR2. Thus, we are considering the possibility that the immunosuppressive effect of SecA2 is due to a role in localization of cell wall synthetic enzymes that influence cell wall architecture. A final possibility is that the ΔsecA2 mutant phenotypes actually represent increased release of a stimulatory molecule (Braunstein et al., 2003).

REFERENCES CITED

Abou-Zeid, C., Smith, I., Grange, J. M., Ratliff, T. L., Steele, J., and Rook, G. A. (1988) The secreted antigens of *Mycobacterium tuberculosis* and their relationship to those recognized by the available antibodies. *J Gen Microbiol* 134 (Pt 2): 531-538.

Adams, L. B., Y. Fukutomi, and J. L. Krahenbuhl. (1993) Regulation of murine macrophage effector functions by lipoarabinomannan from mycobacterial strains with different degrees of virulence. *Infect Immun* 61:4173-81.

Alemán, M. et al. (2002) *Mycobacterium tuberculosis*-induced activation accelerates apoptosis in peripheral blood neutrophils from patients with active tuberculosis. *Am J Respir Cell Mol Biol* 27:583-592.

Andersen, P. (1994) The T cell response to secreted antigens of *Mycobacterium tuberculosis*. *Immunobiology* 191: 537-547.

Armstrong, J. A., and Hart, P. D. (1975) Phagosome-lysosome interactions in cultured macrophages infected with virulent tubercle bacilli. Reversal of the usual nonfusion pattern and observations on bacterial survival. *J Exp Med* 142: 1-16.

Balcewicz-Sablinska, M. K., Keane, J., Komfeld, H. & Remold, H. G. (1998) Pathogenic *Mycobacterium tuberculosis* evades apoptosis of host macrophages by release of TNF-R2, resulting in inactivation of TNF-alpha. *J Immunol* 161: 2636-41.

Bange, F. C., Collins, F. M. & Jacobs, W. R., Jr. (1999) Survival of mice infected with *Mycobacterium smegmatis* containing large DNA fragments from *Mycobacterium tuberculosis*. *Tuber Lung Dis* 79: 171-80.

Bardarov, S. et al. (2002) Specialized transduction: an efficient method for generating marked and unmarked targeted gene disruptions in *Mycobacterium tuberculosis, M. bovis* BCG and *M. smegmatis*. *Microbiology* 148: 3007-17.

Barnes, P. F., D. Chatterjee, J. S. Abrams, S. Lu, E. Wang, M. Yamamura, P. J. Brennan, and R. L. Modlin. (1992) Cytokine production induced by *Mycobacterium tuberculosis* lipoarabinomannan. Relationship to chemical structure. *J Immunol* 149:541-7.

Barry-Lane, P. A., C. Patterson, M. van der Merwe, Z. Hu, S. M. Holland, E. T. Yeh, and M. S. Runge. (2001) p47phox is required for atherosclerotic lesion progression in ApoE (−/−) mice. *J Clin Invest* 108:1513-22.

Battistoni, A. (2003) Role of prokaryotic Cu,Zn superoxide dismutase in pathogenesis. *Biochem Soc Trans* 31:1326-9.

Bean, A. G., D. R. Roach, H. Briscoe, M. P. France, H. Komer, J. D. Sedgwick, and W. J. Britton. (1999) Structural deficiencies in granuloma formation in TNF gene-targeted mice underlie the heightened susceptibility to aerosol *Mycobacterium tuberculosis* infection, which is not compensated for by lymphotoxin. *J Immunol* 162:3504-11.

Beltan, E., L. Horgen, and N. Rastogi. (2000) Secretion of cytokines by human macrophages upon infection by pathogenic and non-pathogenic mycobacteria. *Microb Pathog* 28:313-8.

Bermudez, L. E., and Goodman, J. (1996) *Mycobacterium tuberculosis* invades and replicates within type II alveolar cells. *Infect Immun* 64: 1400-1406.

Berthet, F. X., Lagranderie, M., Gounon, P., Laurent-Winter, C., Ensergueix, D., Chavarot, P., Thouron, F., Maranghi, E., Pelicic, V., Portnoi, D., Marchal, G., and Gicquel, B. (1998) Attenuation of virulence by disruption of the *Mycobacterium tuberculosis* erp gene. *Science* 282: 759-762.

Blanke, S. R. (2005) Micro-managing the executioner: pathogen targeting of mitochondria. *Trends Microbiol* 13: 64-71.

Botha, T., and B. Ryffel. (2003) Reactivation of latent tuberculosis infection in TNF-deficient mice. *J Immunol* 171: 3110-8. SecA homologues function in mycobacteria. *J Bacteriol* 183:6979-90.

Braunstein, M., Griffin, T. I., Kriakov, J. I., Friedman, S. T., Grindley, N. D., and Jacobs, W. R., Jr. (2000) Identification of genes encoding exported *Mycobacterium tuberculosis* proteins using a Tn552'phoA in vitro transposition system. *J Bacteriol* 182: 2732-2740.

Braunstein, M. et al. (2003) SecA2 functions in the secretion of superoxide dismutase A and in the virulence of *Mycobacterium tuberculosis*. *Mol Microbiol* 48: 453-464.

Braunstein, M., A. M. Brown, S. Kurtz, and W. R. Jacobs, Jr. (2001) Two nonredundant Brightbill, H. D., D. H. Libraty, S. R. Krutzik, R. B. Yang, J. T. Belisle, J. R. Bleharski, M. Maitland, M. V. Norgard, S. E. Plevy, S. T. Smale, P. J. Brennan, B. R. Bloom, P. J. Godowski, and R. L. Modlin. (1999) Host defense mechanisms triggered by microbial lipoproteins through toll-like receptors. *Science* 285:732-6.

Byrd, T. F. 1997. Tumor necrosis factor alpha (TNFalpha) promotes growth of virulent *Mycobacterium tuberculosis* in human monocytes iron-mediated growth suppression is correlated with decreased release of TNFalpha from iron-treated infected monocytes. *J Clin Invest* 99:2518-29.

Ciaramella, A. et al. (2000) Mycobacterial 19-kDa lipoprotein mediates *Mycobacterium tuberculosis*-induced apoptosis in monocytes/macrophages at early stages of infection. *Cell Death Differentiation* 7:1270-1272.

Carroll, J. D., Wallace, R. C., Keane, J., Remold, H. G., and Arbeit, R. D. (2000) Identification of *Mycobacterium avium* DNA sequences that encode exported proteins by using phoA gene fusions. *Tuber Lung Dis* 80: 117-130.

Chan, J., Y. Xing, R. S. Magliozzo, and B. R Bloom. (1992) Killing of virulent *Mycobacterium tuberculosis* by reactive nitrogen intermediates produced by activated murine macrophages. *J Exp Med* 175:1111-22.

Clemens, D. L., and Horwitz, M. A. (1995) Characterization of the *Mycobacterium tuberculosis* phagosome and evidence that phagosomal maturation is inhibited. *J Exp Med* 181: 257-270.

Cole, S. T. et al. (1998) Deciphering the biology of *Mycobacterium tuberculosis* from the complete genome sequence. *Nature* 393: 537-44.

Coombes, B. K., Y. Valdez, and B. B. Finlay. (2004) Evasive maneuvers by secreted bacterial proteins to avoid innate immune responses. *Curr Biol* 14:R856-67.

Corbett, E. L., Watt, C. J., Walker, N., Maher, D., Williams, B. G., Raviglione, M. C., and Dye, C. (2003) The growing burden of tuberculosis: global trends and interactions with the HIV epidemic. *Arch Intern Med* 163: 1009-1021.

Daffe, M., and Etienne, G. (1999) The capsule of *Mycobacterium tuberculosis* and its implications for pathogenicity. *Tuber Lung Dis* 79: 153-169.

Dannenberg, A. M., Jr. (1993) Immunopathogenesis of pulmonary tuberculosis. *Hosp Pract (Off Ed)* 28: 51-58.

Dao, D. N. et al. (2004) *Mycobacterium tuberculosis* lipomannan induces apoptosis and interleukin-12 production in macrophages. *Infect Immun* 72: 2067-74.

De Groote, M. A., U. A. Ochsner, M. U. Shiloh, C. Nathan, J. M. McCord, M. C. Dinauer, S. J. Libby, A. Vazquez-Torres, Y. Xu, and F. C. Fang. (1997) Periplasmic superoxide dismutase protects *Salmonella* from products of phagocyte NADPH-oxidase and nitric oxide synthase. *Proc Natl Acad Sci USA* 94:13997-4001.

Duan, L., Gan, H., Arm, J., and Remold, H. G. (2001) Cytosolic phospholipase A2 participates with TNF-alpha in the induction of apoptosis of human macrophages infected with *Mycobacterium tuberculosis* H37Ra. *J Immunol* 166: 7469-7476.

Duan, L. et al. (2002) Critical role of mitochondrial damage in determining outcome of macrophage infection with *Mycobacterium tuberculosis*. *J Immunol* 169:5181-5187.

Duarte, R. et al. (1997) *Mycobacterium tuberculosis* induces apoptosis in δ/γ T lymphocytes from patients with advanced clinical forms of active tuberculosis. *Clin Diag Lab Immunol* 4:14-18.

Dussurget, O., G. Stewart, O. Neyrolles, P. Pescher, D. Young, and G. Marchal. (2001) Role of *Mycobacterium tuberculosis* copper-zinc superoxide dismutase. *Infect Immun* 69:529-33.

Dye, C., Scheele, S., Dolin, P., Pathania, V. & Raviglione, M. C. Consensus statement. (1999) Global burden of tuberculosis: estimated incidence, prevalence, and mortality by country. WHO Global Surveillance and Monitoring Project. *JAMA* 282: 677-86.

Eddine, A. N. and Kaufmann, S. H. E. (2005) Improved protection by recombinant BCG. *Microbes and Infection* 7: 939-946.

Edwards, K. M., Cynamon, M. H., Voladri, R. K., Hager, C. C., DeStefano, M. S., Tham, K. T., Lakey, D. L., Bochan, M. R., and Kernodle, D. S. (2001) Iron-cofactored superoxide dismutase inhibits host responses to *Mycobacterium tuberculosis*. *Am J Respir Crit Care Med* 164: 2213-2219.

Engele, M., E. Stossel, K. Castiglione, N. Schwerdtner, M. Wagner, P. Bolcskei, M. Rollinghoff, and S. Stenger. (2002) Induction of TNF in human alveolar macrophages as a potential evasion mechanism of virulent *Mycobacterium tuberculosis*. *J Immunol* 168:1328-37.

Falcone, V., E. B. Bassey, A. Toniolo, P. G. Conaldi, and F. M. Collins. (1994) Differential release of tumor necrosis factor-alpha from murine peritoneal macrophages stimulated with virulent and avirulent species of mycobacteria. *FEMS Immunol Med Microbiol* 8:225-32.

Fan, S., Wang, J. A., Yuan, R. Q., Rockwell, S., Andres, J., Zlatapolskiy, A., Goldberg, I. D., and Rosen, E. M. (1998) Scatter factor protects epithelial and carcinoma cells against apoptosis induced by DNA-damaging agents. *Oncogene* 17: 131-141.

Finlay, B. B., and Falkow, S. (1997) Common themes in microbial pathogenicity revisited. *Microbiol. Mol Biol Rev* 61: 136-169.

Flesch, I. E., and S. H. Kaufmann. (1990) Activation of tuberculostatic macrophage functions by gamma interferon, interleukin-4, and tumor necrosis factor. *Infect Immun* 58:2675-7.

Flynn, J. L., and J. Chan. (2001) Immunology of tuberculosis. *Annu Rev Immunol* 19:93-129.

Flynn, J. L., M. M. Goldstein, J. Chan, K. J. Triebold, K. Pfeffer, C. J. Lowenstein, R. Schreiber, T. W. Mak, and B. R. Bloom. (1995) Tumor necrosis factor-alpha is required in the protective immune response against *Mycobacterium tuberculosis* in mice. *Immunity* 2:561-72.

Fortune, S. M., A. Jaeger, D. A. Sarracino, M. R Chase, C. M. Sassetti, D. R. Sherman, B. R. Bloom, and E. J. Rubin. (2005) Mutually dependent secretion of proteins required for mycobacterial virulence. *Proc Natl Acad Sci USA* 102: 10676-81.

Fortune, S. M., A. Solache, A. Jaeger, P. J. Hill, J. T. Belisle, B. R. Bloom, E. J. Rubin, and J. D. Ernst. (2004) *Mycobacterium tuberculosis* inhibits macrophage responses to IFN-gamma through myeloid differentiation factor 88-dependent and -independent mechanisms. *J Immunol* 172: 6272-80.

Fratazzi, C., Arbeit, R. D., Carini, C. & Remold, H. G. (1997) Programmed cell death of *Mycobacterium avium* serovar 4-infected human macrophages prevents the mycobacteria from spreading and induces mycobacterial growth inhibition by freshly added, uninfected macrophages. *J Immunol* 158: 4320-7.

Freeman, S., F. A. Post, L. G. Bekker, R. Harbacheuski, L. M. Steyn, B. Ryffel, N. D. Connell, B. N. Kreiswirth, and G. Kaplan. (2006) *Mycobacterium tuberculosis* H37Ra and H37Rv differential growth and cytokine/chemokine induction in murine macrophages in vitro. *J Interferon Cytokine Res* 26:27-33.

Friedrich, T. & Bottcher, B. (2004) The gross structure of the respiratory complex 1: a Lego System. *Biochim Biophys Acta* 1608: 1-9. Gao, L., and Abu Kwaik, Y. (2000) Hijacking of apoptotic pathways by bacterial pathogens. *Microbes Infect* 2: 1705-1719.

Gatfield, J., and Pieters, J. (2000) Essential role for cholesterol in entry of mycobacteria into macrophages. *Science* 288: 1647-1650.

Gehring, A. J., R. E. Rojas, D. H. Canaday, D. L. Lakey, C. V. Harding, and W. H. Boom. (2003) The *Mycobacterium tuberculosis* 19-kilodalton lipoprotein inhibits gamma interferon-regulated HLA-DR and Fc gamma R1 on human macrophages through Toll-like receptor 2. *Infect Immun* 71:4487-97.

Gil, D. P., Leon, L. G., Correa, L. I., Maya, J. R., Paris, S. C., Garcia, L. F., and Rojas, M. (2004) Differential induction of apoptosis and necrosis in monocytes from patients with tuberculosis and healthy control subjects. *J Infect Dis* 189: 2120-2128.

Greer, S. F., E. Zika, B. Conti, X. S. Zhu, and J. P. Ting. (2003) Enhancement of CIITA transcriptional function by ubiquitin. *Nat Immunol* 4:1074-82.

Grode, L. et al. (2005) Increased vaccine efficacy against tuberculosis of recombinant *Mycobacterium bovis* bacilli Calmette-Guérin mutants that secrete listeriolysin. *J Clin Invest* 118:2472-2479.

Guinn, K. M., M. J. Hickey, S. K. Mathur, K. L. Zakel, J. E. Grotzke, D. M. Lewinsohn, S. Smith, and D. R. Sherman. (2004) Individual RD1-region genes are required for export of ESAT-6/CFP-10 and for virulence of *Mycobacterium tuberculosis*. *Mol Microbiol* 51:359-70.

Heldwein, K. A., M. D. Liang, T. K. Andresen, K. E. Thomas, A. M. Marty, N. Cuesta, S. N. Vogel, and M. J. Fenton (2003) TLR2 and TLR4 serve distinct roles in the host immune response against *Mycobacterium bovis* BCG. *J Leukoc Biol* 74:277-86.

Hsu T, et al. (2003) *Proc. Natl. Acad. Sci. USA* 100:12420

Hubbard, R. D., Flory, C. M., and Collins, F. M. (1992) Immunization of mice with mycobacterial culture filtrate proteins. *Clin Exp Immunol* 87: 94-98.

Hussain, S., B. S. Zwilling, and W. P. Lafuse. (1999) *Mycobacterium avium* infection of mouse macrophages inhibits IFN-gamma Janus kinase-STAT signaling and gene induction by down-regulation of the IFN-gamma receptor. *J Immunol* 163:2041-8.

Jang, S., S. Uematsu, S. Akira, and P. Salgame. (2004) IL-6 and IL-10 induction from dendritic cells in response to *Mycobacterium tuberculosis* is predominantly dependent on TLR2-mediated recognition. *J Immunol* 173:3392-7.

Johansen, K. A., Gill, R. E., and Vasil, M. L. (1996) Biochemical and molecular analysis of phospholipase C and phospholipase D activity in mycobacteria. *Infect Immun* 64: 3259-3266.

Karakousis, P. C., W. R. Bishai, and S. E. Dorman. (2004) *Mycobacterium tuberculosis* cell envelope lipids and the host immune response. *Cell Microbiol* 6:105-16.

Keane, J., Balcewicz-Sablinska, M. K., Remold, H. G., Chupp, G. L., Meek, B. B., Fenton, M. J., and Kornfeld, H. (1997) Infection by *Mycobacterium tuberculosis* promotes human alveolar macrophage apoptosis. *Infect Immun* 65: 298-304.

Keane, J., Remold, H. G., and Komfeld, H. (2000) Virulent *Mycobacterium tuberculosis* strains evade apoptosis of infected alveolar macrophages. *J Immunol* 164: 2016-2020.

Komfeld, H. et al. (1999) The role of macrophage cell death in tuberculosis. *Cell Death Differentiation* 6:71-78.

Koul, A., T. Herget, B. Klebl, and A. Ullrich. (2004) Interplay between mycobacteria and host signalling pathways. *Nat Rev Microbiol* 2:189-202.

Kramer, K., Harrington, E. O., Lu, Q., Bellas, R., Newton, J., Sheahan, K. L., and Rounds, S. (2003) Isoprenylcysteine carboxyl methyltransferase activity modulates endothelial cell apoptosis. *Mol Biol Cell* 14: 848-857.

Krutzik, S. R., and R. L. Modlin. (2004) The role of Toll-like receptors in combating mycobacteria. *Semin Immunol* 16:3541.

Kurtz, S., and M. Braunstein. (2005) Protein secretion and export in *Mycobacterium tuberculosis*, p. 71-138. In T. Parish (ed.), *Mycobacterium* Molecular Microbiology. Horizon bioscience.

Leemans, J. C., Juffermans, N. P., Florquin, S., van Rooijen, N., Vervoordeldonk, M. J., Verbon, A., van Deventer, S. J., and van der Poll, T. (2001) Depletion of alveolar macrophages exerts protective effects in pulmonary tuberculosis in mice. *J Immunol* 166: 4604-4611.

Lim, E. M., Rauzier, J., Timm, J., Torrea, G., Murray, A., Gicquel, B., and Portnoi, D. (1995) Identification of *Mycobacterium tuberculosis* DNA sequences encoding exported proteins by using phoA gene fusions. *J Bacteriol* 177: 59-65.

Lopez, M., Sly, L. M., Luu, Y., Young, D., Cooper, H., and Reiner, N. E. (2003) The 19-kDa *Mycobacterium tuberculosis* protein induces macrophage apoptosis through Toll-like receptor-2. *J Immunol* 170: 2409-2416.

Lyadova, I. V. et al. (2000) *J. Immunol* 165:5921-5931.

MacGurn, J. A., S. Raghavan, S. A. Stanley, and J. S. Cox. (2005) A non-RD1 gene cluster is required for 5 nm secretion in *Mycobacterium tuberculosis*. *Mol Microbiol* 57:1653-63.

MacMicking, J., Q. W. Xie, and C. Nathan. (1997a) Nitric oxide and macrophage function. *Annu Rev Immunol* 15:323-50.

MacMicking, J. D., R. J. North, R. LaCourse, J. S. Mudgett, S. K. Shah, and C. F. Nathan. (1997b) Identification of nitric oxide synthase as a protective locus against tuberculosis. *Proc Natl Acad Sci USA* 94:5243-8.

MacMicking, J. D., G. A. Taylor, and J. D. McKinney. (2003) Immune control of tuberculosis by IFN-gamma-inducible LRG-47. *Science* 302:654-9.

Manca, C., S. Paul, C. E. Barry, V. H. Freedman, and G. Kaplan. (1999) *Mycobacterium tuberculosis* catalase and peroxidase activities and resistance to oxidative killing in human monocytes in vitro. *Infec Immunity* 67:74-79.

Manca, C., M. B. Reed, S. Freeman, B. Mathema, B. Kreiswirth, C. E. Barry, 3rd, and G. Kaplan. (2004) Differential monocyte activation underlies strain-specific *Mycobacterium tuberculosis* pathogenesis. *Infect Immun* 72:5511-4.

Molloy, A., Laochumroonvorapong, P., and Kaplan, G. (1994) Apoptosis, but not necrosis, of infected monocytes is coupled with killing of intracellular *bacillus* Calmette-Guerin. *J Exp Med* 180: 1499-1509.

Moore, K. J., and Matlashewski, G. (1994) Intracellular infection by *Leishmania donovani* inhibits macrophage apoptosis. *J Immunol* 152: 2930-2937.

Nagai, S., Wiker, H. G., Harboe, M., and Kinomoto, M. (1991) Isolation and partial characterization of major protein antigens in the culture fluid of *Mycobacterium tuberculosis*. *Infect Immun* 59: 372-382.

Nagabhushanam, V., A. Solache, L. M. Ting, C. J. Escaron, J. Y. Zhang, and J. D. Ernst. (2003) Innate inhibition of adaptive immunity: *Mycobacterium tuberculosis*-induced IL-6 inhibits macrophage responses to IFN-gamma. *J Immunol* 171:4750-7.

Nash, P. B., Pumer, M. B., Leon, R. P., Clarke, P., Duke, R. C., and Curiel, T. J. (1998) *Toxoplasma gondii*-infected cells are resistant to multiple inducers of apoptosis. *J Immunol* 160: 1824-1830.

Nathan, C. (2003) Specificity of a third kind: reactive oxygen and nitrogen intermediates in cell signaling. *J Clin Invest* 111:769-78.

Nau, G. J., J. F. Richmond, A. Schlesinger, E. G. Jennings, E. S. Lander, and R. A. Young. (2002) Human macrophage activation programs induced by bacterial pathogens. *Proc Natl Acad Sci USA* 99:1503-8.

Nauseef, W. M. (2004) Assembly of the phagocyte NADPH oxidase. *Histochem Cell Biol* 122:277-91.

Ng, V. H., J. S. Cox, A. O, Sousa, J. D. MacMicking, and J. D. McKinney. (2004) Role of KatG catalase-peroxidase in mycobacterial pathogenesis: countering the phagocyte oxidative burst. *Mol Microbiol* 52:1291-302.

Nguyen, L. & Pieters, J. (2005) The Trojan horse: survival tactics of pathogenic mycobacteria in macrophages. *Trends Cell Biol* 15: 269-76.

Nicolle, D. M., X. Pichon, A. Bouchot, I. Maillet, F. Erard, S. Akira, B. Ryffel, and V. F. Quesniaux. (2004) Chronic pneumonia despite adaptive immune response to *Mycobacterium bovis* BCG in MyD88-deficient mice. *Lab Invest* 84:1305-21.

North, R. J., and Y. J. Jung. (2004) Immunity to tuberculosis. *Annu Rev Immunol* 22:599-623.

North, R. J. (1995) *Mycobacterium tuberculosis* is strikingly more virulent for mice when given via the respiratory than via the intravenous route. *J Infect Dis* 172: 1550-1553.

Noss, E. H., C. V. Harding, and W. H. Boom. (2000) *Mycobacterium tuberculosis* inhibits MHC class II antigen processing in murine bone marrow macrophages. *Cell Immunol* 201:63-74.

Noss, E. H., Pai, R. K., Sellati, T. J., Radolf, J. D., Belisle, J., Golenbock, D. T., Boom, W. H., and Harding, C. V. (2001) Toll-like receptor 2-dependent inhibition of macrophage class II MHC expression and antigen processing by 19-kDa lipoprotein of *Mycobacterium tuberculosis*. *J Immunol* 167: 910-918.

Oddo, M., Renno, T., Attinger, A., Bakker, T., MacDonald, H. R., and Meylan, P. R. (1998) Fas ligand induced apoptosis of infected human macrophages reduces the viability of intracellular *Mycobacterium tuberculosis*. *J Immunol* 160: 5448-5454.

Orme, I. M. (2003) The mouse as a useful model of tuberculosis. *Tuberculosis (Edinb)* 83: 112-115.

Orme, I. M., and F. M. Collins. (1994) Mouse model of tuberculosis, p. 113-134. In B. R. Bloom (ed.), *Tuberculosis*: Pathogenesis, Protection, and Control. ASM Press, Washington D.C.

Pai, R. K., M. E. Pennini, A. A. Tobian, D. H. Canaday, W. H. Boom, and C. V. Harding. (2004) Prolonged toll-like receptor signaling by *Mycobacterium tuberculosis* and its 19-kilodalton lipoprotein inhibits gamma interferon-induced regulation of selected genes in macrophages. *Infect Immun* 72:6603-14.

Pal, P. G., and Horwitz, M. A. (1992) Immunization with extracellular proteins of *Mycobacterium tuberculosis* induces cell-mediated immune responses and substantial protective immunity in a guinea pig model of pulmonary tuberculosis. *Infect Immun* 60: 4781-4792.

Pan, H. et al. (2005) Ipr1 gene mediates innate immunity to tuberculosis. *Nature* 434: 767-72.

Piddington, D. L., F. C. Fang, T. Laessig, A. M. Cooper, I. M. Orme, and N. A. Buchmeier. (2001) Cu,Zn superoxide dismutase of *Mycobacterium tuberculosis* contributes to survival in activated macrophages that are generating an oxidative burst. *Infect Immun* 69:4980-7.

Portales-Pérez, D. P. et al. (2002) Comparative and prospective study of different immune parameters in healthy subjects at risk for tuberculosis and in tuberculosis patients. *Clin Diag Lab Immunol* 9:299-307.

Quesniaux, V., C. Fremond, M. Jacobs, S. Parida, D. Nicolle, V. Yeremeev, F. Bihl, F. Erard, T. Botha, M. Drennan, M. N. Soler, M. Le Bert, B. Schnyder, and B. Ryffel. (2004a) Toll-like receptor pathways in the immune responses to mycobacteria. *Microbes Infect* 6:946-59.

Quesniaux, V. J., D. M. Nicolle, D. Torres, L. Kremer, Y. Guerardel, J. Nigou, G. Puzo, F. Erard, and B. Ryffel. (2004b) Toll-like receptor 2 (TLR2)-dependent-positive and TLR2-independent-negative regulation of proinflammatory cytokines by mycobacterial lipomannans. *J Immunol* 172:4425-34.

Rao, V., N. Fujiwara, S. A. Porcelli, and M. S. Glickman. (2005) *Mycobacterium tuberculosis* controls host innate immune activation through cyclopropane modification of a glycolipid effector molecule. *J Exp Med* 201:535-43.

Reed, M. B., P. Domenech, C. Manca, H. Su, A. K. Barczak, B. N. Kreiswirth, G. Kaplan, and C. E. Barry, 3rd. (2004) A glycolipid of hypervirulent tuberculosis strains that inhibits the innate immune response. *Nature* 431:84-7.

Reiling, N., C. Holscher, A. Fehrenbach, S. Kroger, C. J. Kirschning, S. Goyert, and S. Ehlers. (2002) Cutting edge: Toll-like receptor (TLR)2- and TLR4-mediated pathogen recognition in resistance to airborne infection with *Mycobacterium tuberculosis*. *J Immunol* 169:3480-4.

Repique, C. J., A. Li, W. J. Brickey, J. P. Ting, F. M. Collins, and S. L. Morris. (2003) Susceptibility of mice deficient in the MHC class II transactivator to infection with *Mycobacterium tuberculosis*. *Scand J Immunol* 58:15-22.

Ricci, J. E. et al. (2004) Disruption of mitochondrial function during apoptosis is mediated by caspase cleavage of the p75 subunit of complex 1 of the electron transport chain. *Cell* 117: 773-86.

Riendeau, C. J., and Komfeld, H. (2003) THP-1 cell apoptosis in response to Mycobacterial infection. *Infect Immun* 71: 254-259.

Roberts, A. D., Sonnenberg, M. G., Ordway, D. J., Furney, S. K., Brennan, P. J., Belisle, J. T., and Orme, I. M. (1995) Characteristics of protective immunity engendered by vaccination of mice with purified culture filtrate protein antigens of *Mycobacterium tuberculosis*. *Immunology* 85: 502-508.

Rojas, M., Barrera, L. F., Puzo, G., and Garcia, L. F. (1997) Differential induction of apoptosis by virulent *Mycobacterium tuberculosis* in resistant and susceptible murine macrophages: role of nitric oxide and mycobacterial products. *J Immunol* 159: 1352-1361.

Rojas, M., Olivier, M., Gros, P., Barrera, L. F., and Garcia, L. F. (1999) TNF-alpha and IL-10 modulate the induction of apoptosis by virulent *Mycobacterium tuberculosis* in murine macrophages. *J Immunol* 162: 6122-6131.

Rojas, M., Garcia, L. F., Nigou, J., Puzo, G., and Olivier, M. (2000) Mannosylated lipoarabinomannan antagonizes *Mycobacterium tuberculosis*-induced macrophage apoptosis by altering Ca+2-dependent cell signaling. *J Infect Dis* 182: 240-251.

Rolls, M. M., Stein, P. A., Taylor, S. S., Ha, E., McKeon, F., and Rapoport, T. A. (1999) A visual screen of a GFP-fusion library identifies a new type of nuclear envelope membrane protein. *J Cell Biol* 146: 29-44.

Rousseau, C., N. Winter, E. Pivert, Y. Bordat, O. Neyrolles, P. Ave, M. Huerre, B. Gicquel, and M. Jackson. (2004) Production of phthiocerol dimycocerosates protects *Mycobacterium tuberculosis* from the cidal activity of reactive nitrogen intermediates produced by macrophages and modulates the early immune response to infection. *Cell Microbiol* 6:277-87.

Sambandamurthy, V. K., Wang, X., Chen, B., Russell, R. G., Derrick, S., Collins, F. M., Morris, S. L., and Jacobs, W. R., Jr. (2002) A pantothenate auxotroph of *Mycobacterium tuberculosis* is highly attenuated and protects mice against tuberculosis. *Nat Med* 8: 1171-1174.

Sassetti, C. M. & Rubin, E. J. (2003) Genetic requirements for mycobacterial survival during infection. *Proc Natl Acad Sci USA* 100: 12989-94.

Saunders, B. M., A. A. Frank, I. M. Orme, and A. M. Cooper. (2000) Interleukin-6 induces early gamma interferon production in the infected lung but is not required for generation of specific immunity to *Mycobacterium tuberculosis* infection. *Infect Immun* 68:3322-6.

Schnappinger, D. et al. (2003) Transcriptional Adaptation of *Mycobacterium tuberculosis* within Macrophages: Insights into the Phagosomal Environment. *J Exp Med* 198: 693-704.

Scanga, C. A., Mohan, V. P., Tanaka, K., Alland, D., Flynn, J. L., and Chan, J. (2001) The inducible nitric oxide synthase locus confers protection against aerogenic challenge of both clinical and laboratory strains of *Mycobacterium tuberculosis* in mice. *Infect Immun* 69: 7711-7717.

Schaible, U. E., Winau, F., Sieling, P. A., Fischer, K., Collins, H. L., Hagens, K., Modlin, R. L., Brinkmann, V., and Kaufmann, S. H. (2003) Apoptosis facilitates antigen presentation to T lymphocytes through MHC-1 and CD I in tuberculosis. *Nat Med* 9: 1039-1046.

Schrijvers D M, Martinet W, De Meyer G R, Andries L, Herman A G, Kockx M M. (2004) *J Immunol Methods* 287: 101-8

Schwebach, J. R., Chen, B., Glatman-Freedman, A., Casadevall, A., McKinney, J. D., Harb, J. L., McGuire, P. J., Barkley, W. E., Bloom, B. R., and Jacobs, W. R., Jr. (2002) Infection of mice with aerosolized *Mycobacterium tuberculosis*: use of a nose-only apparatus for delivery of low doses of inocula and design of an ultrasafe facility. *Appl Environ Microbiol* 68: 4646-4649.

Shi, S., A. Blumenthal, C. M. Hickey, S. Gandotra, D. Levy, and S. Ehrt. (2005) Expression of many immunologically important genes in *Mycobacterium tuberculosis*-infected macrophages is independent of both TLR2 and TLR4 but dependent on IFN-alphabeta receptor and STAT1. *J Immunol* 175:3318-28.

Shi, S., C. Nathan, D. Schnappinger, J. Drenkow, M. Fuortes, E. Block, A. Ding, T. R. Gingeras, G. Schoolnik, S. Akira, K. Takeda, and S. Ehrt. (2003) MyD88 primes macrophages for full-scale activation by interferon-gamma yet mediates few responses to *Mycobacterium tuberculosis*. *J Exp Med* 198:987-97.

Shimono, N., L. Morici, N. Casali, S. Cantrell, B. Sidders, S. Ehrt, and L. W. Riley. (2003) Hypervirulent mutant of *Mycobacterium tuberculosis* resulting from disruption of the mcel operon. *Proc Nail Acad Sci USA* 100:15918-23.

Silver, R. F., Q. Li, and J. J. Ellner. (1998) Expression of virulence of *Mycobacterium tuberculosis* within human monocytes: virulence correlates with intracellular growth and induction of tumor necrosis factor alpha but not with evasion of lymphocyte-dependent monocyte effector functions. *Infect Immun* 66:1190-9.

Sly, L. M., Hingley-Wilson, S. M., Reiner, N. E. & McMaster, W. R. (2003) Survival of *Mycobacterium tuberculosis* in host macrophages involves resistance to apoptosis dependent upon induction of antiapoptotic Bcl-2 family member Mcl-1. *J Immunol* 170: 430-7.

Smith, I. (2003) *Mycobacterium tuberculosis* pathogenesis and molecular determinants of virulence. *Clin Microbiol Rev* 16:463-96.

Snapper, S. B., Melton, R. E., Mustafa, S., Kieser, T. & Jacobs, W. R., Jr. (1990) Isolation and characterization of efficient plasmid transformation mutants of *Mycobacterium smegmatis*. *Mol Microbiol* 4: 1911-9.

Spira, A. et al. (2003) Apoptosis genes in human alveolar macrophages infected with virulent or attenuated *Mycobacterium tuberculosis*. *Am J Respir Cell Mol Biol* 29: 545-551.

Stanley, S. A., S. Raghavan, W. W. Hwang, and J. S. Cox. (2003) Acute infection and macrophage subversion by *Mycobacterium tuberculosis* require a specialized secretion system. *Proc Nail Acad Sci USA* 100:13001-6.

Stenger, S., Niazi, K. R., and Modlin, R. L. (1998) Downregulation of CDI on antigen-presenting cells by infection with *Mycobacterium tuberculosis*. *J Immunol* 161: 3582-3588.

Stover, C. K. et al. (1991) New use of BCG for recombinant vaccines. *Nature* 351: 456-60.

Teodoro, J. G., and Branton, P. E. (1997) Regulation of apoptosis by viral gene products. *J Virol* 71: 1739-1746.

Thannickal, V. J., and B. L. Fanburg. (2000) Reactive oxygen species in cell signaling. *Am J Physiol Lung Cell Mol Physiol* 279:L1005-28.

Underhill, D. M., A. Ozinsky, K. D. Smith, and A. Aderem. (1999) Toll-like receptor-2 mediates mycobacteria-induced proinflammatory signaling in macrophages. *Proc Natl Acad Sci USA* 96:14459-63.

VanHeyningen, T. K., Collins, H. L., and Russell, D. G. (1997) IL-6 produced by macrophages infected with *Mycobacterium* species suppresses T cell responses. *J Immunol* 158: 330-337.

Vaux, D. L., and Strasser, A. (1996) The molecular biology of apoptosis. *Proc Nat Acad Sci USA* 93: 2239-2244.

Wadee, A. A., Kuschke, R. H., and Dooms, T. G. (1995) The inhibitory effects of *Mycobacterium tuberculosis* on MHC class II expression by monocytes activated with rimiphenazines and phagocyte stimulants. *Clin Exp Immunol* 100: 434-439.

Watanabe, Y., and C. O. Jacob. (1991) Regulation of MHC class II antigen expression. Opposing effects of tumor necrosis factor-alpha on IFN-gamma-induced HLA-DR and Ia expression depends on the maturation and differentiation stage of the cell. *J Immunol* 146:899-905.

Wengenack, N. L., M. P. Jensen, F. Rusnak, and M. K. Stem. (1999) *Mycobacterium tuberculosis* KatG is a peroxynitritase. *Biochem Biophys Res Commun* 256:485-487.

Williams, K. L., D. J. Taxman, M. W. Linhoff, W. Reed, and J. P. Ting. (2003) Cutting edge: Monarch-1: a pyrin/nucleotide-binding domain/leucine-rich repeat protein that controls classical and nonclassical MHC class I genes. *J Immunol* 170:5354-8.

World Health Organization 2005. WHO Information tuberculosis fact sheet. [http://www.who.int/mediacentre/factsheets/fs104/en/#global]

Ylid, U., and Wick, M. J. (2000) *Salmonella*-induced apoptosis of infected macrophages results in presentation of a bacteria-encoded antigen after uptake by bystander dendritic cells. *J Exp Med* 191: 613-624.

Zhang, Y., Heym, B., Allen, B., Young, D., and Cole, S. (1992) The catalase-peroxidase gene and isoniazid resistance of *Mycobacterium tuberculosis*. *Nature* 358: 591-593.

Zhang-Barber, L. et al. (1998) Protection of chickens against experimental fowl typhoid using a nuoG mutant of *Salmonella* serotype Gallinarum. *Vaccine* 16:899-903.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

APPENDIX

SEQ ID NOs

SEQ ID NO:1 - coding sequence for amino acid residues 252-269 of chicken ovalbumin
SIINFEKL SEQ ID NO:2 - probe for 18S rRNA
CAAATTACCCACTCCCGACCG SEQ ID NO:3 - forward primer for 18S rRNA
GCTGCTGGCACCAGACTT SEQ ID NO:4 - reverse primer for 18S rRNA
CGGCTACCACATCCAAGG SEQ ID NO:5 - probe for murine MHC class II (I-Ab)
CGCAGCGCATACGATATGTGACCA SEQ ID NO:6 - reverse primer for murine MHC class II (I-Ab)
CTGTCGTAGCGCACGTACT SEQ ID NO:7 - forward primer for murine MHC class II (I-Ab)
GGCGAGTGCTACTTCACCA SEQ ID NO:8 - probe for human MHC class II (HLA-DRA)
CTGGACCCTTTGCAAGAACCCTTCCC SEQ ID NO:9 - forward primer for human MHC class II (HLA-DRA)
TCCAATGAACGGAGTATCTTGTGT SEQ ID NO:10 - reverse primer for human MHC class II (HLA-DRA)
TGAGATGACGCATCTGTTGCT

What is claimed is:

1. An isolated mycobacterium comprising
(a) a mutation in a gene of the mycobacterium controlling production of an amino acid which renders the mycobacterium auxotrophic for lysine; and
(b) a mutation in a SecA2 gene, wherein the mutation eliminates SecA2 activity, wherein the mycobacterium is an *M. tuberculosis* or an *M. bovis* BCG.

2. The mycobacterium of claim 1, wherein the mycobacterium is an *M. bovis* BCG.

3. The mycobacterium of claim 1, wherein the mycobacterium is an *M. tuberculosis*.

4. The mycobacterium of claim 1, wherein at least one of the mutations was made by genetic engineering methods.

5. The mycobacterium of claim 1, further comprising a recombinant gene encoding an antigen of a mammalian pathogen operably linked to a promoter that directs expression of the gene when the mycobacterium infects a mammalian cell.

6. The mycobacterium of claim 5, wherein the pathogen is a virus.

7. The mycobacterium of claim 5, wherein the pathogen is a bacterium.

8. The mycobacterium of claim 5, wherein the pathogen is a eukaryotic parasite.

9. The mycobacterium of claim 5, wherein the mammalian pathogen is a human pathogen.

10. The mycobacterium of claim 6, wherein the virus is HIV, hepatitis C, herpes, influenza, smallpox, diphtheria, tetanus, measles, mumps, rabies or polio virus.

11. The mycobacterium of claim 7, wherein the bacterium is a pathogenic mycobacteria or *Salmonella* sp.

12. The mycobacterium of claim 8, wherein the eukaryotic parasite is malaria or *Leishmania*.

13. An isolated mycobacterium comprising
(a) a deletion of the gene encoding nlaA having the sequence set forth in SEQ ID NO:11; and
(b) a mutation in a SecA2 gene, wherein the mutation eliminates SecA2 activity, wherein the mycobacterium is an *M. tuberculosis* or an *M. bovis* BCG.

14. The mycobacterium of claim 13, wherein the mycobacterium is an *M. bovis* BCG.

15. The mycobacterium of claim 13, wherein the mycobacterium is an *M. tuberculosis.*

16. The mycobacterium of claim 13, wherein at least one of the mutations was made by genetic engineering methods.

17. The mycobacterium of claim 13, further comprising a recombinant gene encoding an antigen of a mammalian pathogen operably linked to a promoter that directs expression of the gene when the mycobacterium infects a mammalian cell.

18. The mycobacterium of claim 17, wherein the pathogen is a virus.

19. The mycobacterium of claim 17, wherein the pathogen is a bacterium.

20. The mycobacterium of claim 17, wherein the pathogen is a eukaryotic parasite.

21. The mycobacterium of claim 17, wherein the mammalian pathogen is a human pathogen.

22. The mycobacterium of claim 18, wherein the virus is HIV, hepatitis C, herpes, influenza, smallpox, diphtheria, tetanus, measles, mumps, rabies or polio virus.

23. The mycobacterium of claim 19, wherein the bacterium is a pathogenic mycobacteria or *Salmonella* sp.

24. The mycobacterium of claim 20, wherein the eukaryotic parasite is malaria or *Leishmania.*

* * * * *

SEQUENCE LISTING

<160> NUMBER OF SEQ ID NOS: 12

<210> SEQ ID NO 1
<211> LENGTH: 8
<212> TYPE: PRT
<213> ORGANISM: Chicken

<400> SEQUENCE: 1

Ser Ile Ile Asn Phe Glu Lys Leu
1               5

<210> SEQ ID NO 2
<211> LENGTH: 21
<212> TYPE: DNA
<213> ORGANISM: ARTIFICIAL SEQUENCE
<220> FEATURE:
<223> OTHER INFORMATION: Probe directed to human 18S rRNA

<400> SEQUENCE: 2
caaattaccc actcccgacc g                                           21

<210> SEQ ID NO 3
<211> LENGTH: 18
<212> TYPE: DNA
<213> ORGANISM: ARTIFICIAL SEQUENCE
<220> FEATURE:
<223> OTHER INFORMATION: Primer directed to human 18s rRNA

<400> SEQUENCE: 3
gctgctggca ccagactt                                               18

<210> SEQ ID NO 4
<211> LENGTH: 18
<212> TYPE: DNA
<213> ORGANISM: ARTIFICIAL SEQUENCE
<220> FEATURE:
<223> OTHER INFORMATION: Primer directed to human 18s rRNA

<400> SEQUENCE: 4
cggctaccac atccaagg                                               18

<210> SEQ ID NO 5
<211> LENGTH: 24
<212> TYPE: DNA
<213> ORGANISM: ARTIFICIAL SEQUENCE
<220> FEATURE:
<223> OTHER INFORMATION: Probe directed to murine MHC

<400> SEQUENCE: 5
cgcagcgcat acgatatgtg acca                                        24

<210> SEQ ID NO 6
<211> LENGTH: 19
<212> TYPE: DNA
<213> ORGANISM: ARTIFICIAL SEQUENCE
<220> FEATURE:
<223> OTHER INFORMATION: Primer directed to murine MHC

<400> SEQUENCE: 6
ctgtcgtagc gcacgtact                                              19

<210> SEQ ID NO 7
<211> LENGTH: 19
<212> TYPE: DNA
<213> ORGANISM: Artificial Sequence

```
<220> FEATURE:
<223> OTHER INFORMATION: Probe for human MHC

<400> SEQUENCE: 7
ggcgagtgct acttcacca                                                19

<210> SEQ ID NO 8
<211> LENGTH: 26
<212> TYPE: DNA
<213> ORGANISM: Artificial Sequence
<220> FEATURE:
<223> OTHER INFORMATION: Primer for human MHC

<400> SEQUENCE: 8
ctggaccctt tgcaagaacc cttccc                                        26

<210> SEQ ID NO 9
<211> LENGTH: 24
<212> TYPE: DNA
<213> ORGANISM: Artificial Sequence
<220> FEATURE:
<223> OTHER INFORMATION: Primer directed to human MHC

<400> SEQUENCE: 9
tccaatgaac ggagtatctt gtgt                                          24

<210> SEQ ID NO 10
<211> LENGTH: 21
<212> TYPE: DNA
<213> ORGANISM: Artificial Sequence
<220> FEATURE:
<223> OTHER INFORMATION: Primer directed to human MHC

<400> SEQUENCE: 10
tgagatgacg catctgttgc t                                             21

<210> SEQ ID NO 11
<211> LENGTH: 244
<212> TYPE: PRT
<213> ORGANISM: Mycobacterium tuberculosis

<400> SEQUENCE: 11

Met Lys Arg Tyr Leu Thr Ile Ile Tyr Gly Ala Ala Ser Tyr Leu Val
1               5                   10                  15

Phe Leu Val Ala Phe Gly Tyr Ala Ile Gly Phe Val Gly Asp Val Val
            20                  25                  30

Val Pro Arg Thr Val Asp His Ala Ile Ala Ala Pro Ile Gly Gln Ala
        35                  40                  45

Val Val Val Asn Leu Val Leu Leu Gly Val Phe Ala Val Gln His Ser
    50                  55                  60

Val Met Ala Arg Gln Gly Phe Lys Arg Trp Trp Thr Arg Phe Val Pro
65                  70                  75                  80

Pro Ser Ile Glu Arg Ser Thr Tyr Val Leu Leu Ala Ser Val Ala Leu
                85                  90                  95

Leu Leu Leu Tyr Trp Gln Trp Arg Thr Met Pro Ala Val Ile Trp Asp
            100                 105                 110

Val Arg Gln Pro Ala Gly Arg Val Ala Leu Trp Ala Leu Phe Trp Leu
        115                 120                 125

Gly Trp Ala Thr Val Leu Thr Ser Thr Phe Met Ile Asn His Phe Glu
    130                 135                 140

Leu Phe Gly Leu Arg Gln Val Tyr Leu Ala Trp Arg Gly Lys Pro Tyr
145                 150                 155                 160
```

```
Thr Glu Ile Gly Phe Gln Ala His Leu Leu Tyr Arg Trp Val Arg His
                165                 170                 175
Pro Ile Met Leu Gly Phe Val Val Ala Phe Trp Ala Thr Pro Met Met
            180                 185                 190
Thr Ala Gly His Leu Leu Phe Ala Ile Gly Ala Thr Gly Tyr Ile Leu
        195                 200                 205
Val Ala Leu Gln Phe Glu Glu Arg Asp Leu Leu Ala Ala Leu Gly Asp
    210                 215                 220
Gln Tyr Arg Asp Tyr Arg Arg Glu Val Ser Met Leu Leu Pro Trp Pro
225                 230                 235                 240
His Arg His Thr

<210> SEQ ID NO 12
<211> LENGTH: 735
<212> TYPE: DNA
<213> ORGANISM: Mycobacterium tuberculosis

<400> SEQUENCE: 12
atgaagcgtt atttgacgat catttacggg ccgcgagct atctggtatt cctggttgcc      60
ttcgggtatg cgatcggttt cgtcggcgac gtagtggtgc cacgaaccgt agatcacgcg     120
atcgcggcgc cgatcggcca ggcggtcgtg gtcaacttgg tgctgctggg cgtgttcgcc     180
gtccaacata gcgtgatggc acgacagggt ttcaaacgct ggtggactcg attcgtgccg     240
ccctcgatcg agcgcagcac ctatgtactg ctggccagcg ttgcgctgtt gttgctgtac     300
tggcaatggc gaacgatgcc ggcggtcatc tgggacgtgc ggcagccggc tggccgggtg     360
gcgttgtggg cgttgttctg gctcgggtgg gccacggtgt tgacgtcgac tttcatgatc     420
aatcatttcg aattgttcgg cctacggcag gtgtatttgg cttggcgcgg aaagccgtac     480
accgagatcg gttttcaggc tcatctgctc taccggtggg tacgccaccc gatcatgctc     540
ggattcgtcg tcgcgttctg ggcgacgccc atgatgacgg cggggcactt gcttttcgcg     600
atcggcgcga cgggctacat cttggtcgcg ttgcagttcg aagagcgcga cctactcgcg     660
gcgctgggcg accaataccg cgattaccgc cgcgaggtgt cgatgttgtt gccgtggccg     720
caccggcata cctga                                                      735
```